United States Patent [19]

Smith et al.

[11] Patent Number: 4,849,513
[45] Date of Patent: Jul. 18, 1989

[54] DEOXYRIBONUCLEOSIDE PHOSPHORAMIDITES IN WHICH AN ALIPHATIC AMINO GROUP IS ATTACHED TO THE SUGAR RING AND THEIR USE FOR THE PREPARATION OF OLIGONUCLEOTIDES CONTAINING ALIPHATIC AMINO GROUPS

[75] Inventors: Lloyd M. Smith, South Pasadena; Steven Fung, Palo Alto, both of Calif.

[73] Assignee: California Institute of Technology, Pasadena, Calif.

[21] Appl. No.: 878,045

[22] Filed: Jun. 24, 1986

Related U.S. Application Data

[63] Continuation-in-part of Ser. No. 565,010, Dec. 20, 1983, abandoned, and Ser. No. 709,579, Mar. 8, 1985, abandoned.

[51] Int. Cl.$^4$ .................... C07H 19/10; C07H 19/20
[52] U.S. Cl. ........................................ 536/27; 536/28; 536/29
[58] Field of Search .............................. 536/27, 28, 29

[56] References Cited

U.S. PATENT DOCUMENTS 4,668,777  5/1987  Caruthers .............................. 536/28

FOREIGN PATENT DOCUMENTS 0063879 10/1982 European Pat. Off. .............. 536/23
0090789 10/1983 European Pat. Off. .............. 536/23
86/06726 11/1986 PCT Int'l Appl. .................. 536/23
86/07361 12/1986 PCT Int'l Appl. .................. 536/29

OTHER PUBLICATIONS

Fourrey et al., Chemical Abstracts, vol. 104, 1986, 130215a.
Tanaka et al., Chemical Abstracts, vol. 106, 1987, 33420x.

*Primary Examiner*—Johnnie R. Brown
*Assistant Examiner*—Jenny Tou
*Attorney, Agent, or Firm*—Joseph E. Mueth

[57] ABSTRACT

The invention consists of compounds and methods for the synthesis of oligonucleotides which contain one or more free aliphatic amino groups attached to the sugar moieties of the nucleoside subunits. The synthetic method is versatile and general, permitting amino groups to be selectively placed at any position on oligonucleotides of any composition or length which is attainable by current DNA synthetic methods. Fluorescent dyes or other detectable moieties may be covalently attached to the amino groups to yield the corresponding modified oligonucleotide.

67 Claims, No Drawings

DEOXYRIBONUCLEOSIDE PHOSPHORAMIDITES IN WHICH AN ALIPHATIC AMINO GROUP IS ATTACHED TO THE SUGAR RING AND THEIR USE FOR THE PREPARATION OF OLIGONUCLEOTIDES CONTAINING ALIPHATIC AMINO GROUPS

This is a continuation-in-part of U.S. patent application Ser. Nos. 565,010, filed Dec. 20, 1983 and 709,579, filed Mar. 8, 1985, both now abandoned.

BACKGROUND OF THE INVENTION

An oligonucleotide is a short polymer consisting of a linear sequence of four nucleotides in a defined order. The nucleotide subunits are joined by phosphodiester linkages joining the 3'-hydroxyl moiety of one nucleotide to the 5'-hydroxyl moiety of the next nucleotide. An example of an oligonucleotide is 5'>ApCpGp-TpApTpGpGpC<3'. The letters A, C, G, and T refer to the nature of the purine or pyrimidine base coupled at the 1'-position of deoxyribose: A, adenine; C, cytosine; G, guanine; and T, thymine. "p" represents the phosphodiester bond. The chemical structure of a section of an oligonucleotide is shown in FIG. 1.

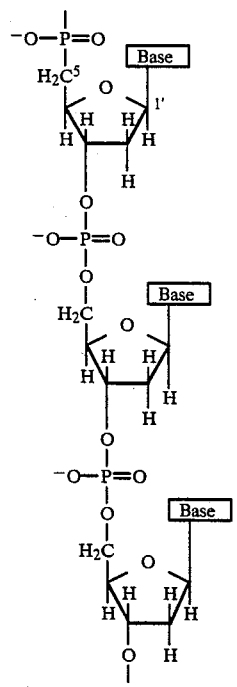

Figure 1
Structure of part of a DNA chain.
This figure is taken from the text book Biochemistry, by Lubert Styer, First Edition 1975, W. H. Freeman & Co., page 558.

Synthetic oligonucleotides are powerful tools in modern molecular biology and recombinant DNA work. There are numerous applications for these molecules, including (a) as probes for the isolation of specific genes based on the protein sequence of the gene product, (b) to direct the in vitro mutagenesis of a desired gene, (c) as primers for DNA synthesis on a single-stranded template, (d) as steps in the total synthesis of genes, and many more, reviewed in Wm. R. Bahl et al, *Prog. Nucl. Acid Res. Mol. Biol.* 21, 101, (1978).

A very considerable amount of effort has therefore been devoted to the development of efficient chemical methods for the synthesis of such oligonucleotides. A brief review of these methods as they have developed to the present is found in Crockett, G. C., *Aldrichimica Acta* 16(3), 47–55 (1983), and "Oligonucleotide Synthesis: A Practical Approach", ed. Gait, M. J., IRL Press, Oxford, England (1984). The best methodology currently available utilizes the phosphoramidite derivatives of the nucleosides in combination with a solid phase synthetic procedure, Matteucci, M. D. and Caruthers, M. H. *J. Am. Chem. Soc.* 103, 3185, (1981); and Beaucage, S. L., and Caruthers, M. H., *Tet. Lett.* 22(20), 1858–1862 (1981). In this chemistry, the 3'-nucleoside of the sequence to be synthesized is attached to a solid support via a base-labile linker arm. Subsequent nucleosides are attached sequentially to the previous nucleoside to generate a linear polymer of defined sequence extending off of the solid support. The general structure of a deoxyribonucleoside phosphoramidite is shown in FIG. 2:

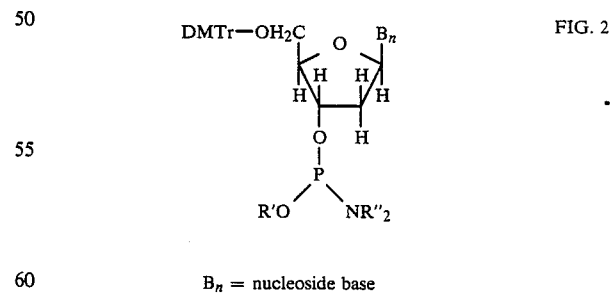

FIG. 2

$B_n$ = nucleoside base

DMTr = di-p-anisylphenylmethyl
(also known as dimethoxytrityl)

and the chemical steps used in each cycle of oligonucleotide synthesis are shown in FIG. 3:

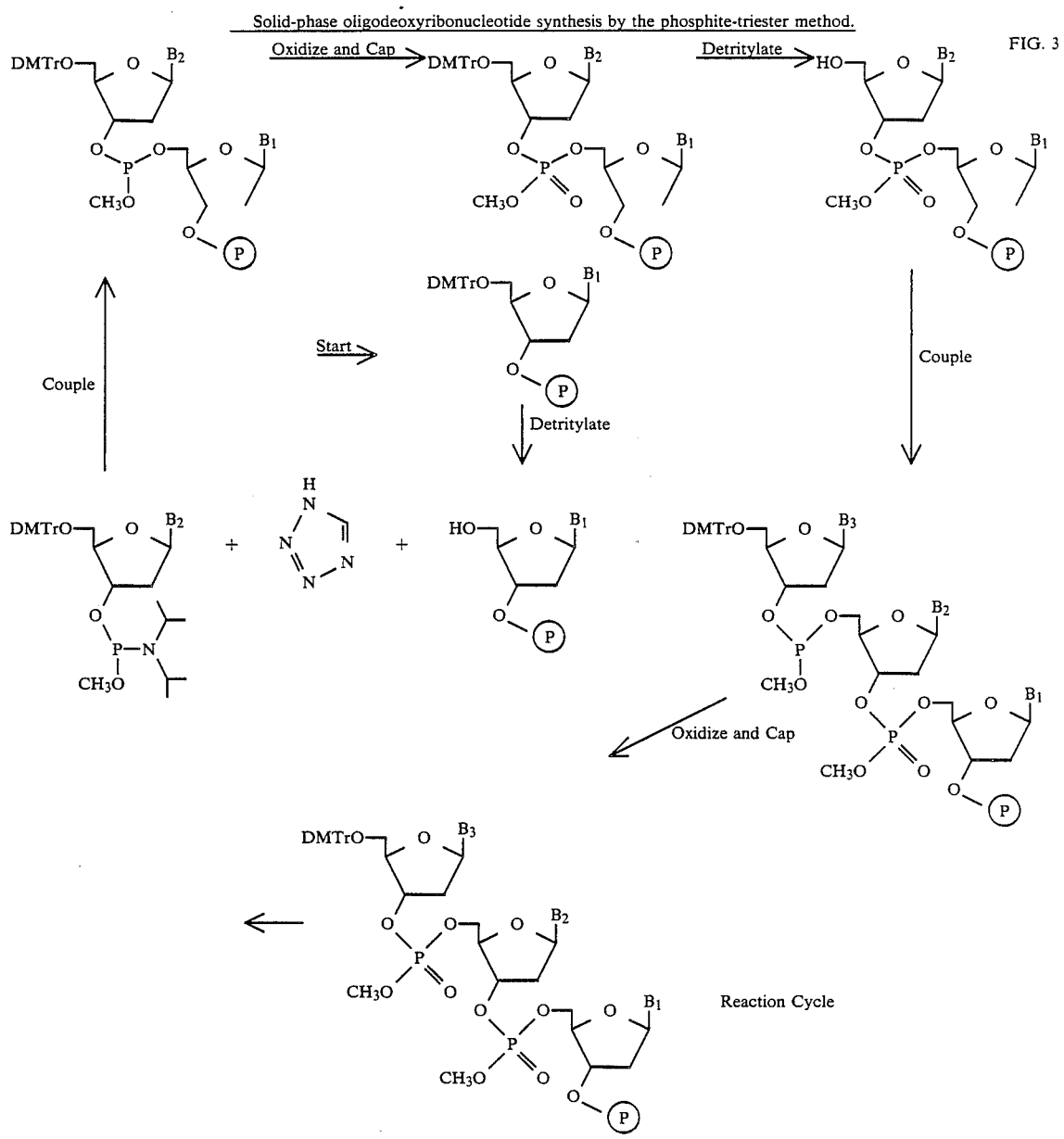

Solid-phase oligodeoxyribonucleotide synthesis by the phosphite-triester method.

$B_1$, $B_2$, $B_3$ = $A^{Bz}$, $C^{Bz}$, $G^{iBu}$ or T (P): Derivatized Support (This FIG. is taken from "Oligonucleotide Synthesis: a Practical Approach", ed. Gait, M. J., IRL Press (1984), p. 37)

Oligonucleotides of length up to 40 bases may be made on a routine basis in this manner, and molecules as long as 106 bases have been made. Machines that employ this chemistry are now commercially available.

There are many reasons to want a method for covalently attaching other chemical species to synthetic oligonucleotides. Fluorescent dyes attached to the oligonucleotides permit one to eliminate radioisotopes from the research, diagnostic, and clinical procedures in which they are used, and improve shelf-life and availability. As described in the assignees co-pending application for a DNA sequencing machine Ser. No. 570,973, filed Jan. 16, 1984) the synthesis of fluorescent-labeled oligonucleotides permits the automation of the DNA sequencing process. The development of appropriate techniques and instrumentation for the detection and use of fluorescent-labeled oligonucleotides allows the automation of other currently laborious laboratory and clinical techniques. The attachment of DNA cleavage chemicals such as those disclosed by Schultz et al, J. Am. Chem. Soc. 104, 6861 (1982); and Hertzberg, R. P., and Dervan, P. B., J. Am. Chem. Soc. 104, 313 (1982) permits the construction of synthetic restriction enzymes, whose specificity is directed by the oligonucleotide sequence.

There are several reports in the literature of the derivitization of DNA. A modified nucleoside triphosphate has been developed wherein a biotin group is conjugated to an aliphatic amino group at the 5-position of uracil, Langer et al., *Proc. Nat. Acad. Sci. U.S.A.* 78, 6633-6637 (1981). This nucleotide derivative is effectively incorporated into double stranded DNA in a process referred to as "nick translation." Once in DNA it may be bound by anti-biotin antibody which can then be used for detection by fluorescence or enzymatic methods. The DNA which has had biotin-conjugated nucleosides incorporated therein by the method of Langer et al is fragmented into smaller single and double stranded pieces which are heterogeneous with respect to the sequence of nucleoside subunits and variable in molecular weight. Draper and Gold, *Biochemistry* 19, 1774-1781 (1980), reported the introduction of aliphatic amino groups by a bisulfite catalyzed transamination reaction, and their subsequent reaction with a fluorescent tag. In Draper and Gold the amino group is attached directly to a pyrimidine base. The amino group so positioned inhibits hydrogen bonding and for this reason, these materials are not useful in hybridization and the like. Also, this method does not permit amino groups to be inserted selectively at a desired position. Chu et al, *Nucleic Acids Res.* 11(18), 6513-6529 (1983), have reported a method for attaching an amine to the terminal 5'-phosphate of oligonucleotides or nucleic acids. This method involves a number of sequential reaction and purification steps which are laborious to perform and difficult to scale up. It also is restricted to the introduction of a single amino group at the 5'-terminus of the oligonucleotide. Subsequent to the filing of the original patent application of which the present case is a continuation-in-part, Takeda and Ikeda, *Nucl. Acids Res. Symp. Series* 15, 101-104 (1984) have reported the synthesis and use of phosphotriester derivatives of putrescinyl thymidine for the preparation of amino-derivatized oligonucleotides. These materials differ from those reported herein in that the amino containing moiety is attached to the base moiety and not to the sugar moiety of the oligonucleotides, and also in that the DNA synthetic chemistry used was phosphotriester and not phosphoramidite.

The present invention presents a general method for the introduction of one or more free aliphatic amino groups into synthetic oligonucleotides. These groups may be selectively inserted at any desired position in the oligonucleotide. They are readily and specifically reacted with a variety of amino reactive functionalities, and thereby permit the covalent attachment of a wide variety of chemical species in a position specific manner. This is illustrated by the preparation of a number of fluorescent oligonucleotide derivatives. The materials prepared in this fashion are effective in DNA hybridization methods, as illustrated by their use as primers in DNA sequence analysis, and also by a study of their melting behaviour in DNA duplex formation.

According to the present invention, aliphatic amino groups are introduced into an oligonucleotide by first synthesizing a 3'-O-phosphoramidite derivative of a nucleoside analogue containing a protected aliphatic amino group attached to the sugar moiety of the nucleoside. This phosphoramidite is then reacted with the oligonucleotide being synthesized on a solid support. If the amino protecting group is base-labile, the process of oligonucleotide cleavage from the solid phase and deprotection of the base moieties and aliphatic amino group yields the amino-derivatized oligonucleotide. If the amino protecting group is acid-labile, it may be removed by treatment with anhydrous or aqueous acid prior to cleavage of the oligonucleotide from the support and deprotection of the base moieties, or it may be retained during cleavage and deprotection to simplify an improve the chromatographic purification of the oligonucleotide, and then removed subsequently by treatment with aqueous acid, yielding the amino-derivatized oligonucleotide in either case.

More specifically, the present invention concerns modified deoxynucleoside phosphoramidites in which an aliphatic amino group, which has been suitably protected, is attached to the sugar moiety of the nucleoside. The chemical structure of a typical nucleoside is shown in FIG. 4.

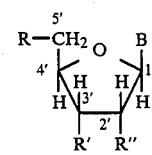

FIG. 4

It is characterized by a heterocyclic pyrimidine or purine base (B) linked by a carbon-nitrogen bond to the furanose (sugar) ring of ribose ($R=R'=R''=OH$) or deoxyribose ($R=R'=OH$; $R''=H$). The numbering of the sugar carbon atoms is 1' to 5' as indicated in the figure; thus, the base is connected to C-1' of the sugar. An aliphatic amino group may be attached in principle to any of the five ring carbons. It also comprises the respective phosphoramidite derivatives which are synthesized by reacting an appropriate phosphine with the free 3'-hydroxyl group of the suitably protected amino nucleosides.

SUMMARY OF THE INVENTION

Briefly, our invention includes novel protected amino nucleosides having the formula:

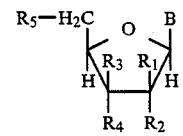

FIG. 5 wherein B is a common nucleoside purine or pyrimidine base, such as adenine, guanine, thymine, cytosine, uracil, or hypoxanthine, or their protected derivatives, especially those currently used in DNA chemical synthesis, namely $N^6$-Benzoyladenine, $N^2$-isobutyrylguanine, $N^4$-benzoylcytosine, $N^6$-di-n-butylformamidinyladenine, $N^6$-(N-methyl-2-pyrrolidineamidinyl)-adenine, $N^6$-succinyladenine, $N^6$-phthaloyladenine, $N^6$-dimethylacetamidinyladenine, or $N^2$-di-n-butylformamidinylguanine; or an uncommon purine or pyrimidine base, such as purine, isocytosine, or xanthine (3,7-dihydro-1H-purine-2,6-dione), or their protected derivatives; or a substituted purine or pyrimidine base. Such substituents include, but are not limited to cyano, halo, haloalkyl, carboxy, formyl, hydroxy, alkoxy, aryl, azido, mercapto, nitro, carboxy esters, and carboxamides. Such bases include, but are not limited to, 6-chloropurine, 6-chloro-2-fluoropurine, 2,6-diaminopurine, 2-fluoro-$N^6$-hydroxyadenine, 2,6-dihydroxyaminopurine, 8-bromoadenine, 2-chloroadenine, 8-azidoadenine, 8-mercaptoadenine, 8-aminoadenine, 6-thioguanine, 2,6-dichloropurine, N,N-dimethyl-6-aminopurine, $N^6$-benzyladenine, 1,3-dimethylxanthine, 2-amino-6,8-dihydroxypurine, 6-methoxypurine, 6-mercaptopurine, 6-(2-hydroxyethyl)-aminopurine, $N^6$-(2-isopentyl)-adenine, $N^6$-furfuryladenine (kinetin), 5-bromomethyluracil, 5-dibromomethyluracil, 5-hydroxymethyluracil, 5-formyluracil, 5-fluorouracil, 5-bromouracil, 6-methyl-2-thiouracil, 5-hydroxymethyl-6-methyluracil, 5-hydroxyuracil (isobarbituric acid), 5-methoxyuracil, 5-methylcytosine, 5-trifluoromethyluracil, 5-nitrouracil, 5-aminouracil, 2-thiocytosine, 2-amino-4,6-dihydroxypyrimdine, 4-amino-2,6-dihydroxypyrimidine, 2-amino-4-hydroxy-6-methylpyrimidine, or 4-amino-6-hydroxy-2-mercaptopyrimidine, or their protected derivatives.

B may also be a nucleoside base analog; such analogs are molecules that mimic the normal purine or pyrimidine bases in that their structures (the kinds of atoms and their arrangement) are similar to the normal bases, but may either possess additional or lack certain of the functional properties of the normal bases; such base analogues include, but are not limited to, imidazole and its 2-,4-, and/or 5-substituted derivatives (substituents are as defined above), indole and its 2-,3-,4-,5-,6-, and/or 7-substituted derivatives, benzimidazole and its 2-,4-,5-,6-, and/or 7-substituted derivatives, indazole and its 3-,4-,5-,6-, and/or 7-substituted derivatives, pyrazole and its 3-,4-, and/or 5-substituted derivatives, triazole and its 4- and/or 5-substituted derivatives, tetrazole and its 5-substituted derivatives, benzotriazole and its 4-,5-,6-, and/or 7-substituted derivatives, 8-azaadenine and its substituted derivatives, 8-azaguanine and its substituted derivatives, 6-azathymine and its substituted derivatives, 6-azauracil and its substituted derivatives, 5-azacytosine and its substituted derivatives, 8-azahypoxanthine and its substituted derivatives, pyrazolopyrimidine and its substituted derivatives, 3-deazauracil, orotic acid (2,6-dioxo-1,2,3,6-tetrahydro-4-pyrimidine carboxylic acid), barbituric acid, uric acid, ethenoadenine, and allopurinol (4-hydroxy-pyrazolo [3,4-d]pyrimidine), or their protected derivatives.

B can also be a "C-nucleoside", in which the normal C-N bond between the base and C-1' of the sugar is replaced by a C—C bond; such bases include, but are not limited to, uracil (in the C-nucleoside pseudouridine), 1-methyluracil, 1,3-dimethyluracil, 5(4)-carbomethoxy-1,2,3-triazole, 5(4)-carboxamido-1,2,3-triazole, 3(5)-carboxymethylpyrazole, 3(5)-carbomethoxypyrazole, 5-carboethoxy-1-methylpyrazole, maleimide (in the C-nucleoside showdomycin), and 3(4)-carboxamido-4(3)-hydroxypyrazole (in the C-nucleoside pyrazomycin), or their protected derivatives.

In FIG. 5, $R_1$, $R_2$, $R_3$, $R_4$ and $R_5$ (sometimes collectively referred to as $R_n$) are defined as follows: $R_3$=H, $R_4$=OH, and $R_1$, $R_2$ and $R_5$ are either H, OR, or NHR', wherein R and R' are appropriate protecting groups; R is generally a lower alkyl or aryl ether, such as methyl, t-butyl, benzyl, o-nitrobenzyl, p-nitrobenzyl, o-nitrophenyl, or triphenylmethyl, or a lower alkyl or aryl ester, such as acetyl, benzoyl, or p-nitrobenzoyl, or an alkyl acetal, such as tetrahydropyranyl, or a silyl ether, such trimethylsilyl or t-butyl-dimethylsilyl, or a sulfonic acid ester, such as p-toluenesulfonyl or methanesulfonyl; R' is any common, standard nitrogen protecting group, such as those commonly used in peptide synthesis (R. Geiger and W. Konig, in "The Peptides: Analysis, Synthesis, Biology", E. Gross and J. Meienhofer, eds., v. 3, Academic Press, New York (1981), pp. 1–99); this includes, but is not limited to, acid-labile protecting groups such as formyl, t-butyloxycarbonyl, benzyloxycarbonyl, 2-chlorobenzyloxycarbonyl, 4-chlorobenzyloxycarbonyl, 2-4-dichlorobenzyloxycarbonyl, furfuryloxycarbonyl, t-amyloxycarbonyl, adamantyloxycarbonyl, 2-phenylpropyl (2)oxycarbonyl, 2-(4-biphenyl)propyl(2)oxycarbonyl, triphenylmethyl, p-anisyldiphenylmethyl, di-p-anisylphenylmethyl, 2-nitrophenylsulfenyl, or diphenylphosphinyl; base labile protecting groups such as trifluoroacetyl, 9-fluorenylmethyloxycarbonyl, 4-toluene-sulfonylethyloxycarbonyl, methylsulfonylethyloxycarbonyl, and 2-cyano-t-butyloxycarbonyl; and others, such as chloroacetyl, acetoacetyl, 2-nitro-benzoyl, dithiasuccinoyl, maleoyl, isonicotinyl, 2-bromoethyloxycarbonyl, and 2,2,2-trichloroethyloxycarbonyl.

At most one of $R_1$, $R_2$ and $R_5$ may be NHR', and only $R_4$ may be OH.

The "R" protecting groups referred to hereinabove, when containing carbon atoms, can contain from 1 to about 25 carbon atoms.

CASES (1) If $R_1$=NHR', then $R_2$=H; $R_5$ may be either OR or H; the molecule in this case is termed a protected 2'-amino-2'-deoxyarabinonucleoside.

(2) If $R_2$=NHR', then $R_1$=H; $R_5$ may either be OR or H; the molecule in this case is termed a protected 2'-amino-2'-deoxyribonucleoside.

(3) If $R_5'$=NHR', then either $R_1$ or $R_2$ may be OR, with the other being H, or both may be H; if $R_1$ is OR, the molecule is termed a protected 5'-aminoarabinonucleoside; if $R_2$ is OR, the molecule is termed a protected 5'-amino-ribonucleoside; if both $R_1$ and $R_2$ are H, the molecule is termed a protected 5'-amino 2'-deoxyribonucleoside.

The invention further includes novel phosphoramidites having the formula:

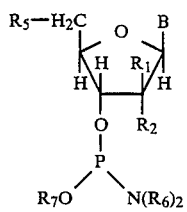

FIG. 6 wherein B, $R_1$, $R_2$ and $R_5$ are as defined above, $R_6$=lower alkyl, preferably lower alkyl such as methyl or isopropyl, or heterocyclic, such as morpholino, pyrrolidino, or 2,2,6,6-tetramethylpyrrolidino, $R_7$=methyl, beta-cyanoethyl, p-nitrophenethyl, o-chlorophenyl, or p-chlorophenyl.

Once again, the "R" groups referred to hereinabove, when containing carbon atoms, can contain from 1 to about 25 carbon atoms.

It must be noted that the moiety symbolized by "B" in FIG. 5 must also be appropriately protected prior to synthesis of the phosphoramidite symbolized by FIG. 6, in order to render the phosphoramidite compatible with the DNA chain assembly chemistry. Such protection is thoroughly discussed in Gait, "Oligonucleotide Synthesis: A Practical Approach", and generally involves acylation or amidination of the exocyclic amino groups of "B"; such acyl groups include, but are not limited to, acetyl, benzoyl, isobutyryl, succinyl, phthaloyl, or p-anisoyl; such amidine groups include, but are not limited to dimethylformamidine, di-n-butylformamidine, or dimethylacetamidine; if "B" is substituted with other reactive groups, such as carboxyl, hydroxyl, or mercapto, these are appropriately protected as well.

In another aspect, this invention comprehends the synthesis of oligonucleotides on a solid phase support, wherein the oligonucleotide is reacted with the protected amino-derivatized nucleoside phosphoramidite of FIG. 6.

In addition, this invention includes the novel oligonucleotides having inserted therein at least one amino-derivatized nucleoside via phosphoramidite precursor of FIG. 6.

The present invention still further comprises the aforementioned novel aliphatic amino-derivatized single stranded oligonucleotides conjugated to a detectable moiety which is a chromophore, fluorescent agent, protein, enzyme, radioactive atom such as $I^{125}$, or other "tag".

It is an object of this invention to provide novel protected nucleosides.

It is yet another object of this invention to provide novel phosphoramidites.

In another important aspect of this invention, it is an object to provide novel oligonucleotides bound to a solid support which have been reacted with the aforementioned phosphoramidites.

It is still another object of this invention to provide novel tagged oligonucleotides which are readily detectable by standard detection means.

These and other objects and advantages of our invention will be apparent to those skilled in the art from the more elaborate and detailed description which follows.

DETAILED DESCRIPTION OF THE INVENTION

The following citations comprise a list of syntheses of amino nucleoside starting materials used in the preparation of the compounds of FIG. 5 hereinabove.

(I) Synthesis of 5'-amino-5'-deoxythymidine and 5'-amino-5'-deoxyuridine and appropriate intermediates (embodiment of case 3):

1. Horwitz, J. P., Tomson, A. J., Urbanski, J. A., and Chua, J., *J. Am. Chem. Soc.* 27, 3045-3048 (1962).

(II) Synthesis of 2'-amino-2'-deoxyuridine and 2'-amino-2'-deoxycytidine and appropriate intermediates (embodiment of case 2):

1. Verheyden, J. P. H., Wagner, D., and Moffatt, J. G., *J. Org. Chem.* 36, 250-254 (1971).
2. Imazawa, M., and Eckstein, F., *J. Org. Chem.* 44, 2039-2041 (1979).
3. Torrence, P. F., and Witkop, B., in "Nucleic Acid Chemistry", vol. 2, Townsend, L. B., and Tipson, R. S., eds., pp. 977-989, J. Wiley and Sons, New York (1978).
4. Sasaki, T., Minamoto, K., Sugiura, T., and Niwa, M., *J. Org. Chem.* 41, 3138-3143 (1976).

(III) Synthesis of 2'-amino-2'-deoxyadenosine and 2'-amino-2'-deoxyguanosine and appropriate intermediates (embodiment of case 2):

1. Imazawa, M., and Eckstein, F. *J. Org. Chem.* 44, 2039-2041 (1979).
2. Hobbs, J. B., and Eckstein, F., *J. Org. Chem.* 42, 714-719 (1976).
3. Ranganathan, R., *Tetrahedron Lett.* 15, 1291-1294 (1977).

4. Mengel, R., and Wiedner, H., *Chem. Ber.* 109, 433-443 (1976).
5. Wolfrom, M. L., and Winkley, M. W., *J. Org. Chem.* 32, 1823-1825 (1967).
6. Ikehara, M., Maruyama, T., and Miki, H., *Tetrahedron Lett.* 49, 4485-4488 (1976).
7. Ikehara, M., and Maruyama, T., *Chem. Pharm. Bull. Japan* 26, 240-244 (1978).

(IV) Synthesis of some C-nucleoside analogs of natural nucleosides (relevant to all cases):

1. De Las Heras, F. G., Tam, S. Y-K., Klein, R. S., and Fox, J. J., *J. Org. Chem.* 41, 84-90 (1976).
2. Trummlitz, G., Repke, D. B., and Moffatt, J. G., *J. Org. Chem.* 40, 3352-3356 (1975).
3. Chu, C. K., Reichman, U., Watanabe, K. A., and Fox, J. J., *J. Heterocyclic Chem.* 14, 1119-1121 (1977).
4. Ogawa, T., Pernet, A. G., and Hanessian, S., *Tetrahedron Lett.* 37, 3543-3546 (1973).
5. "Nucleosides, Nucleotides, and Their Biological Applications", J. L. Rideout, D. W. Henry, and L. M. Beacham III, eds., Academic Press, New York (1983).

(V) Synthesis of amino sugars and amino nucleosides by glycosylation and transglycosidation reactions (relevant to all cases):

1. Azuma, T., and Ishono, K., *Chem. Pharm., Bull. Japan* 25, 3347-3353 (1977).
2. Hashizume, T., and Iwamura, H., *Tetrahedron Lett.* 35, 3095-3102 (1965).
3. Anisuzzaman, A. K. M., and Whistler, R. L., *J. Org. Chem.* 37, 3187-3189 (1972).
4. Bishop, C. T., and Cooper, F. P., *Can. J. Chem.* 41, 2743-2758 (1963).
5. Unger, F. M., Christian, R., and Waldstatten, P., *Tetrahedron Lett.* 50, 4383-4384 (1977).
6. Unger, F. M., Christian, R., and Waldstatten, P., *Tetrahedron Lett.* 7, 605-608 (1979).
7. Bobek, M., and Martin, V., *Tetrahedron Lett.* 22, 1919-1922 (1978).
8. Wolfrom, M. L., Shafizadeh, F., Armstrong, R. K., and Shen Han, T. M., *J. Am. Chem. Soc.* 81, 3716-3719 (1959).
9. Wolfrom, M. L., Shafizadeh, F., and Armstrong, R. K., *J. Am. Chem. Soc.* 80, 4885-4888 (1958).
10. Wulff, G., Rohle, G., and Kruger, W., *Angew. Chem.* 82, 455-456 (1970).
11. Schroeder, L. R., and Green, J. W., *J. Chem Soc. C*, 530-531 (1966).

A preferred class of compounds within the scope of FIG. 5 is given by the following.

Composition of Matter No. 1: 5'-N-protected derivatives of 5'-amino-5'-deoxythymidine having the generic formula:

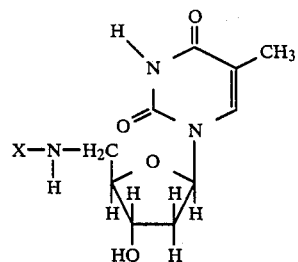

wherein X=a standard nitrogen protecting group as defined in the generic description of the invention accompanying FIG. 5; preferably, X=trifluoroacetyl (Tfa), 9-fluorenylmethyloxycarbonyl (Fmoc), triphenylmethyl (trityl), or p-anisyldiphenylmethyl (also referred to as monomethoxytrityl, MMT).

The formula also encompasses a related class of compounds formed by reacting the compound wherein X=H with an activated appropriately protected amino acid derivative; in this case, X is represented by X=Y—NH—(CHQ)$_n$—CO, wherein Y=a standard nitrogen protecting group as defined for X hereinabove, especially those listed as preferable for X hereinabove; and Q=any common amino acid side chain, with n=1 to about 12; generally n<=6; for n=1, Q includes, but is not limited to, such moieties as H (from the amino acid glycine), methyl (from the amino acid alanine), isopropyl (valine), benzyl (phenylalanine), p-hydroxybenzyl (tyrosine), carboxymethyl (aspartic acid), carboxyethyl (glutamic acid), 4-aminobutyl (lysine), imidazolylmethyl (histidine), indolylmethyl (tryptophan), mercaptomethyl (cystine), or hydroxymethyl (serine); for n>1, Q is generally H: for example, when n=2, the corresponding amino acid is beta-alanine; when n=3, 4-aminobutyric acid; when n=5, 6-aminohexanoic acid. If Q contains reactive moieties such as OH, SH, $CO_2H$, or $NH_2$, these are also appropriately protected with standard groups (see Geiger and Konig, "The Peptides: Analysis: Synthesis, Biology", for a thorough description of such groups). In this class of compounds, the protected amino group is spatially removed from the sugar ring of the nucleoside, either to improve its reactivity or to spatially separate the DNA chain from the "tag" that is to be affixed to the amino group.

The formula also encompasses a class of compounds related to this latter class by having more than one amino acid linked in linear fashion (termed a peptide) attached to the compound wherein X=H; in this case, X is represented by X=Y—[NH—(CHQ$_i$)$_n$—CO]$_m$, wherein Y and n arae as defined hereinabove, the various Q$_i$ are as defined for Q hereinabove, with i=1 to the maximum value of m, and m=1 to about 100; m=1 represents the class defined in the paragraph above.

EXAMPLES

The synthesis of the 5'-O-p-toluenesulfonylthymidine, 5'-azido-5'-deoxythymidine, and 5'-amino-5'-deoxythymidine starting materials are given in:

Horwitz, J. P., Tomson, A. J., Urbanski, J. A., and Chua, J., *J. Org. Chem.* 27, 3045–3048 (1962).

EXAMPLE 1

5'-N-trifluoroacetyl-5'-amino-5'-deoxythymidine having the formula:

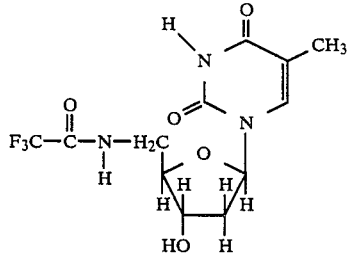

5'-amino-5'-deoxythymidine (1.25 g, 5.0 mmoles) was dissolved in dry N,N-dimethylformamide (DMF) (25 ml). To this solution was added S-ethylthioltrifluoroacetate (1.3 ml, 10 mmoles; Aldrich Chemical Company). The reaction was gently stirred at room temperature. Thin layer chromatography (TLC) of the reaction mixture on silica gel 60 F-254 plates developed in acetone:methanol (1:1 v/v) showed a single spot of product by short wave UV. The product has a high mobility in this solvent system in contrast to the virtually immobile starting aminothymidine.

The reaction mixture was rotary evaporated to dryness under reduced pressure, transferred to an Erlenmeyer flask with 2-propanol (30 ml), and recrystallized from boiling 2-propanol:methanol. Yield: 1.315 g (3.9 mmoles, 80% yield), mp. 261°–262° C.; analysis, 42.7%; H, 4.16%; N, 12.4%. The structure of the product was further confirmed by $^1$H nuclear magnetic resonance (NMR) spectroscopy.

Similarly, the following compounds are prepared:
(1) 5'-N-trifluoroacetyl-5'-amino-2',5'-dideoxy-N$^6$-benzoyladenosine from 5'-amino-2',5'-dideoxy-N$^6$-benzoyladenosine.
(2) 5'-N-trifluoroacetyl-5'-amino-2',5'-dideoxy-N$^2$-isobutyrylguanosine from 5'-amino-2',5'-dideoxy-N$^2$-isobutyrylguanosine.
(3) 5'-N-trifluoroacetyl-5'-amino-2',5'-dideoxy-N$^4$-benzoylcytidine from 5'-amino-2',5'-dideoxy-N$^4$-benzoylcytidine.
(4) 5'-N-trifluoroacetyl-5'-amino-2',5'-dideoxyuridine from 5'-amino-2',5'-dideoxyuridine.
(5) 5'-N-trifluoroacetyl-5'-amino-2',5'-dideoxyinosine from 5'-amino-2',5'-dideoxyinosine.
(6) 5'-N-trifluoroacetyl-5'-amino-2'-tetrahydropyranyl-5'-deoxyuridine from 5'-amino-2'-tetrahydropyranyl-5'-deoxyuridine.
(7) 5'-N-trifluoroacetyl-5'-amino-2'-tetrahydropyranyl-5'-deoxyinosine from 5'-amino-2'-tetrahydropyranyl-5'-deoxyinosine.
(8) 5'-N-trifluoroacetyl-5'-amino-2'-tetrahydropyranyl-N$^6$-benzoyl-5'-deoxyadenosine from 5'-amino-2'-tetrahydropyranyl-N$^6$-benzoyl-5'-deoxyadenosine.
(9) 5'-N-trifluoroacetyl-5'-amino-2'-tetrahydropyranyl-N$^4$-benzoyl-5'-deoxycytosine from 5'-amino-2'-tetrahydropyranyl-N$^4$-benzoyl-5'-deoxycytosine.
(10) 5'-N-trifluoroacetyl-5'-amino-2'-tetrahydropyranyl-N$^2$-isobutyryl-5'-deoxyguanosine from 5'-amino-2'-tetrahydropyranyl-N$^2$-isobutyryl-5'-deoxyguanosine.

EXAMPLE 2

5'-N-(9-fluorenylmethyloxycarbonyl)-5'-amino-5'-deoxythymidine having the formula:

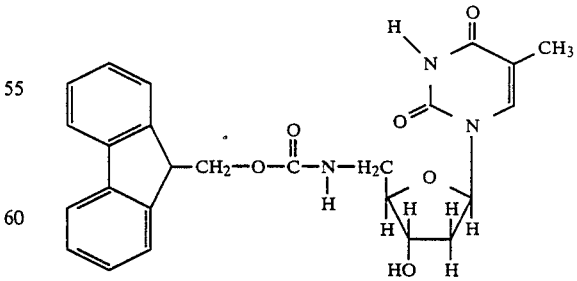

Dry N,N-diisopropylethylamine (0.4 ml, 2.3 mmoles; Aldrich Chemical Company) was combined with dry DMF (3 ml) in a small round bottomed flask. 5'-amino-5'-deoxythymidine (0.5 g, 2.1 mmoles) was suspended in the mixture and 9-fluorenylmethylchloroformate (0.64 g, 2.5 mmoles; Aldrich Chemical Company) was added with stirring. The reaction rapidly became clear and TLC analysis on silica gel 60 F-254 plates developed in chloroform:ethanol:triethylamine (88:10:2 v/v) with short wave UV detection showed a single major spot of product and only a trace of unreacted starting aminothymidine. The productwwas precipitated by the addition of 1M aqueous sodium bicarbonate (25 ml), filtered, and the solid washed several times with, successively, 1M sodium bicarbonate, water, and a mixture of diethyl ether and hexanes (1:1 v/v). The product was dried overnight in a vacuum dessicator to give 0.88 g (1.9 mmoles, 90% yield) of a white solid. In some cases, the product was further purified by crystallization from absolute ethanol. The structure of the product was further confirmed by $^1$H NMR spectroscopy.

Similarly, the following compounds are prepared:
(1) 5'-N-(9-fluorenylmethyloxycarbonyl)-5'-amino-2',5'-dideoxy-N$^6$-benzoyladenosine from 5'-amino-2',5'-dideoxy-N$^6$-benzoyl-adenosine.
(2) 5'-N-(9-fluorenylmethyloxycarbonyl)-5'-amino-2',5-dideoxy-N$^2$-isobutyrylguanosine from 5'-amino-2',5'-dideoxy-N$^2$-isobutyrylguanosine.
(3) 5'-N-(9-fluorenylmethyloxycarbonyl)-5'-amino-2',5'-dideoxy-N$^4$-benzoylcytidine from 5'-amino-2',5'-dideoxy-N$^4$-benzoylcytidine.
(4) 5'-N-(9-fluorenylmethyloxycarbonyl)-5'-amino-2',5'-dideoxyuridine from 5'-amino-2',5'-dideoxyuridine.
(5) 5'-N-(9-fluorenylmethyloxycarbonyl)-5'-amino-2',5'-dideoxyinosine from 5'-amino-2',5'-dideoxyinosine.
(6) 5'-N-(9-fluorenylmethyloxycarbonyl)-5'-amino-2'-tetrahydropyranyl-5'-deoxyuridine from 5'-amino-2'-tetrahydropyranyl-5'-deoxyuridine.
(7) 5'-N-(9-fluorenylmethyloxycarbonyl)-5'-amino-2'-tetrahydropyranyl-5'-deoxyinosine from 5'-amino-2'-tetrahydropyranyl-5'-deoxyinosine.
(8) 5'-N-(9-fluorenylmethyloxycarbonyl)-5'-amino-2'-tetrahydropyranyl-N$^6$-benzoyl-5'-deoxyadenosine from 5'-amino-2'-tetrahydropyranyl-N$^6$-benzoyl-5'-deoxyadenosine.
(9) 5'-N-(9-fluorenylmethyloxycarbonyl)-5'-amino-2'-tetrahydropyranyl-N$^4$-benzoyl-5'-deoxycytosine from 5'-amino-2'-tetrahydropyranyl-N$^4$-benzoyl-5'-deoxycytosine.
(10) 5'-N-(9-fluorenylmethyloxycarbonyl)-5'-amino-2'-tetrahydropyranyl-N$^2$-isobutyryl-5'-deoxyguanosine from 5'-amino-2'-tetrahydropyranyl-N$^2$-isobutyryl-5'-deoxyguanosine.

EXAMPLE 3

5'-N-p-anisyldiphenylmethyl-5'-amino-5'-deoxythymidine having the formula:

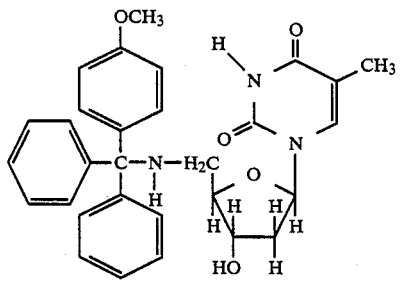

5'-amino-5'-deoxythymidine (2.41 g, 10 mmoles) was coevaporated twice with anhydrous pyridine (25 ml each time) and then suspended in anhydrous pyridine (100 ml). Triethylamine (2.1 ml), N,N-dimethylaminopyridine (0.80 mg; Aldrich Chemical Company), and p-anisylchlorodiphenylmethane (4.68 g, 15.2 mmoles; Aldrich Chemical Company) were added. The reaction mixture was protected from moisture and light, and the yellow-orange solution stirred overnight at room temperature. The reaction was then cooled in ice, and cold saturated aqueous sodium bicarbonate (100 ml) was added to decompose excess tritylating agent. After thirty minutes, the mixture was transferred to a one liter separatory funnel and was extracted twice with ethyl acetate (200 ml portions). The combined ethyl acetate layers were washed twice with water (100 ml portions) and once with saturated aqueous sodium chloride (100 ml), dried over anhydrous magnesium sulfate, filtered, and rotary evaporated to dryness under reduced pressure. The gummy orange-yellow product was then coevaporated twice with anhydrous toluene (100 ml portions) to remove residual pyridine. The residue was dissolved in a minimum amount of ethyl acetate and applied to a column (100 cm by 3.0 cm) of neutral alumina (activity grade V, 15% water by weight; Woelm Pharma GmbH and Company) packed in hexanes. The column was first eluted with ethyl acetate:hexanes (1:1 v/v) until almost all of the bright yellow material had been eluted from the column, and then with pure ethyl acetate. The fractions containing product were pooled and rotary evaporated to dryness. The nearly colorless gummy residue was dissolved in a small volume of ethyl acetate and precipitated into hexanes (400 ml) at room temperature. The product was filtered and dried in a vacuum dessicator to give 4.53 g (8.8 mmoles, 88%) of a white powder, not crystallized. TLC analysis of the purified product on silica gel LQ6DF plates (Pierce Chemical Company) developed in acetonitrile:water (9:1 v/v) showed one spot by short wave UV detection, $R_f$ 0.87, that gave an orange-yellow color characteristic of the p-anisyldiphenylmethyl cation after spraying the plate with perchloric acid:ethanol solution (3:2 v/v). The structure of the product was further confirmed by $^1$H NMR spectroscopy in perdeuterated dimethyl sulfoxide (Merck Isotopes).

Similarly, the following compounds are prepared:
(1) 5'-N-p-anisyldiphenylmethyl-5'-amino-2',5'-dideoxy-N$^6$-benzoyladenosine from 5'-amino-2',5'-dideoxy-N$^6$-benzoyl-adenosine.
(2) 5'-N-p-anisyldiphenylmethyl-5'-amino-2',5'-dideoxy-N$^2$-isobutyrylguanosine from 5'-amino-2',5'-dideoxy-N$^2$-isobutyrylguanosine.
(3) 5'-N-p-anisyldiphenylmethyl-5'-amino-2',5'-dideoxy-N$^4$-benzoylcytidine from 5'-amino-2',5'-dideoxy-N$^4$-benzoylcytidine.
(4) 5'-N-p-anisyldiphenylmethyl-5'-amino-2',5'-dideoxyuridine from 5'-amino-2',5'-dideoxyuridine.
(5) 5'-N-p-anisyldiphenylmethyl-5'-amino-2',5'-dideoxyinosine from 5'-amino-2',5'-dideoxyinosine.
(6) 5'-N-(p-anisyldiphenylmethyl)-5'-amino-2'-tetrahydropyranyl-5'-deoxyuridine from 5'-amino-2'-tetrahydropyranyl-5'-deoxyuridine.
(7) 5'-N-(p-anisyldiphenylmethyl)-5'-amino-2'-tetrahydropyranyl-5'-deoxyinosine from 5'-amino-2'-tetrahydropyranyl-5'-deoxyinosine.
(8) 5'-N-(p-anisyldiphenylmethyl)-5'-amino-2'-tetrahydropyranyl-N$^6$-benzoyl-5'-deoxyadenosine from 5'-amino-2'-tetrahydropyranyl-N$^6$-benzoyl-5'-deoxyadenosine.

(9) 5'-N-(p-anisyldiphenylmethyl)-5'-amino-2'-tetrahydropyranyl-$N^4$-benzoyl-5'-deoxycytosine from 5'-amino-2'-tetrahydropyranyl-$N^4$-benzoyl-5'-deoxycytosine.
(10) 5'-N-(p-anisyldiphenylmethyl)-5'-amino-2'-tetrahydropyranyl-$N^2$-isobutyryl-5'-deoxyguanosine from 5'-amino-2'-tetrahydropyranyl-$N^2$-isobutyryl-5'-deoxyguanosine.
(11) 5'-N-triphenylmethyl-5'-amino-2',5'-dideoxy-$N^6$-benzoyladenosine from 5'-amino-2',5'-dideoxy-$N^6$-benzoyladenosine.
(12) 5'-N-triphenylmethyl-5'-amino-2',5'-dideoxy-$N^2$-isobutyrylguanosine from 5'-amino-2',5'-dideoxy-$N^2$-isobutyrylguanosine.
(13) 5'-N-triphenylmethyl-5'-amino-2',5'-dideoxy-$N^4$-benzoylcytidine from 5'-amino-2',5'-dideoxy-$N^4$-benzoylcytidine.
(14) 5'-N-triphenylmethyl-5'-amino-2',5'-dideoxyuridine from 5'-amino-2',5'-dideoxyuridine.
(15) 5'-N-triphenylmethyl-5'-amino-2',5'-dideoxyinosine from 5'-amino-2',5'-dideoxyinosine.
(16) 5'-N-triphenylmethyl-5'-amino-2'-tetrahydropyranyl-5'-deoxyuridine from 5'-amino-2'-tetrahydropyranyl-5'-deoxyuridine.
(17) 5'-N-triphenylmethyl-5'-amino-2'-tetrahydropyranyl5'-deoxyinosine from 5'-amino-2'-tetrahydropyranyl5'-deoxyinosine.
(18) 5'-N-triphenylmethyl-5'-amino-2'-tetrahydropyranyl-$N^6$-benzoyl-5'-deoxyadenosine from 5'-amino-2'-tetrahydropyranyl-$N^6$-benzoyl-5'-deoxyadenosine.
(19) 5'-N-triphenylmethyl-5'-amino-2'-tetrahydropyranyl-$N^4$-benzoyl-5'-deoxycytosine from 5'-amino-2'-tetrahydropyranyl-$N^4$-benzoyl-5'-deoxycytosine.
(20) 5'-N-triphenylmethyl-5'-amino-2'-tetrahydropyranyl-$N^2$-isobutyryl-5'-deoxyguanosine from 5'-amino-2'-tetrahydropyranyl-$N^2$-isobutyryl-5'-deoxyguanosine.

EXAMPLE 4

5'-N-(N-benzyloxycarbonyl-6-aminohexanoyl)-5'-amino-5'-deoxythymidine having the formula:

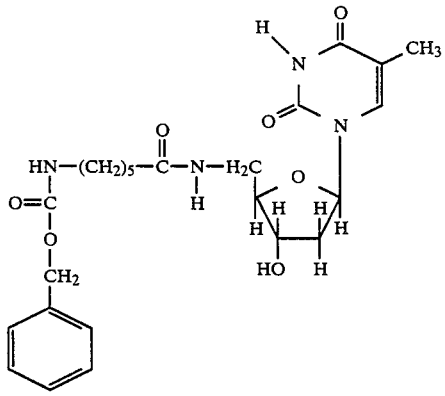

5'-amino-5'-deoxythymidine (1.21 g, 5.0 mmoles) and N-benzyloxycarbonyl-6-aminohexanoic acid p-nitrophenyl ester (2.12 g, 5.5 mmoles; see note below) were dissolved in anhydrous DMF (25 ml) and stirred three days at room temperature. The solution was then rotary evaporated to dryness under reduced pressure to give a yellow solid, which was extensively triturated under several changes of dry ethyl ether. The powdery white product was then filtered, washed well with diethyl ether, and dried in a vacuum dessicator to give 2.31 g (4.7 mmoles, 95%).

Note: N-benzyloxycarbonyl-6-aminohexanoic acid p-nitrophenyl ester was synthesized by standard techniques from N-benzyloxycarbonyl-6-aminohexanoic acid (Sigma Chemical Company), p-nitrophenol (Aldrich Chemical Company), and $N,N^1$-dicyclohexylcarbodiimide (Aldrich Chemical Company) in ethyl acetate solution.

Similarly, the following compounds are prepared:
(1) 5'-N-(N-benzyloxycarbonyl-6-aminohexanoyl)-5'-amino-2',5'-dideoxy-$N^6$-benzoyladenosine from 5'-amino-2',5'-dideoxy-$N^6$-benzoyl-adenosine.
(2) 5'-N-(N-benzyloxycarbonyl-6-aminohexanoyl)-5'-amino-2',5'-dideoxy-$N^2$-isobutyrylguanosine from 5'-amino-2',5'-dideoxy-$N^2$-isobutyrylguanosine.
(3) 5'-N-(N-benzyloxycarbonyl-6-aminohexanoyl)-5'-amino-2',5'-dideoxy-$N^4$-benzoylcytidine from 5'-amino-2',5'-dideoxy-$N^4$-benzoylcytidine.
(4) 5'-N-(N-benzyloxycarbonyl-6-aminohexanoyl)-5'-amino-2',5'-dideoxyuridine from 5'-amino-2',5'-dideoxyuridine.
(5) 5'-N-(N-benzyloxycarbonyl-6-aminohexanoyl)-5'-amino-2',5'-dideoxyinosine from 5'-amino-2',5'-dideoxyinosine.
(6) 5'-N-(N-benzyloxycarbonyl-6-aminohexanoyl)-5'-amino-2'-tetrahydropyranyl-5'-deoxyinosine from 5'-amino-2'-tetrahydropyranyl-5'-deoxyinosine.
(7) 5'-N-(N-benzyloxycarbonyl-6-aminohexanoyl)-5'-amino-2'-tetrahydropyranyl-$N^2$-isobutyryl-5'-deoxyguanosine from 5'-amino-2'-tetrahydropyranyl-$N^2$-isobutyryl-5'-deoxyguanosine.
(8) 5'-N-(N-benzyloxycarbonyl-6-aminohexanoyl)-5'-amino-2',5'-dideoxyuridine from 5'-amino-2',5'-dideoxyuridine.

Composition of Matter No. 2: 3'-O-phosphoramidites of compounds described in composition of matter No. 1 having the generic formula:

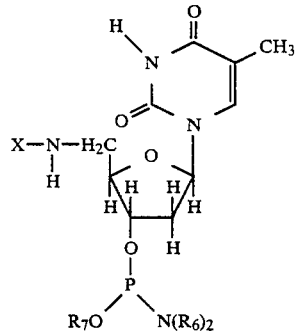

wherein
X=as defined in previous section (composition of matter No. 1),
$R_6$=a lower alkyl, preferably a lower alkyl such as methyl or isopropyl, or a non-aromatic nitrogen-containing heterocycle, such as morpholino, piperidino, pyrrolidino or 2,2,6,6-tetramethylpiperidino,
$R_7$=methyl, beta-cyanoethyl, p-nitrophenethyl, o-chlorophenyl, or p-chlorophenyl.

EXAMPLES

NOTE: The phosphine starting materials used to synthesize the following phosphoramidite compounds were prepared according to literature procedures:

(1) McBride, L. J., and Caruthers, M. H., *Tetrahedron Lett.* 24, 245-248 (1983); and (2) Sinha, N. D., Biernat, J., McManus, J., and Koster, H., *Nucl. Acids Res.* 12. 4539-4557 (1984).

EXAMPLE 5

5'-N-(9-fluorenylmethyloxycarbonyl)-5'-amino-5'-deoxythymidine-3'-O-methyl-N,N-diisopropylamino phosphoramidite having the formula:

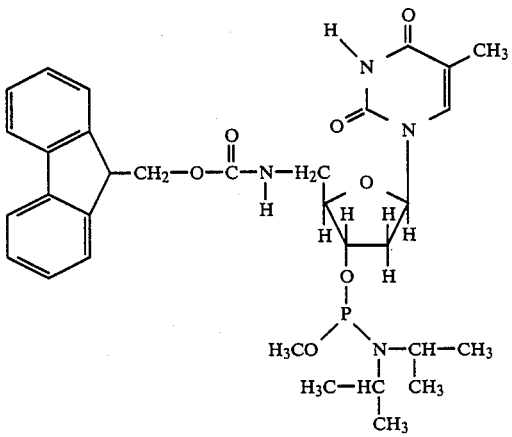

5'-N-(9-fluorenylmethyloxycarbonyl)-5'-amino-5'-deoxythymidine (0.88 g, 1.9 mmoles) was suspended in dry dichloromethane (14 ml, dried by distillation from phosphorous pentoxide then calcium hydride). To this mixture was added N,N-diisopropylethylamine (0.5 ml, 2.9 mmoles). The suspension was stirred at room temperature under a dry argon atmosphere, and chloro-N,N-diisopropylaminomethoxyphosphine (0.4 ml, 2.1 mmoles) was added dropwise from a syringe. The solid starting material gradually dissolved, and TLC on silica gel 60 F-254 plates developed in chloroform:methanol: triethylamine (88:10:2 v/v) using short wave UV detection indicated that the reaction had gone to completion after sixty minutes. Ethyl acetate (50 ml) was added, and the organic phase was washed twice with cold saturated aqueous sodium bicarbonate (50 ml portions) and once with cold saturated aqueous sodium chloride (50 ml), dried over anhydrous magnesium sulfate, filtered, and the solvent removed by rotary evaporation under reduced pressure to yield a white foam (1.20 g, 100% crude yield). The product could be precipitated by dissolving it in few ml of dry toluene and adding this solution dropwise to several hundred ml of hexane at −78° C. (dry ice/acetone bath). The resulting white powder was obtained in 85-95% yield after precipitation and drying in a vacuum dessicator. The structure of the product was confirmed by $^1$H NMR spectroscopy. Phosphorous ($^{31}$P) NMR spectroscopy in perdeuterated acetonitrile (Aldrich Chemical Company) showed two singlets at 148.77 and 148.34 ppm (relative to phosphoric acid in perdeuterated acetonitrile) as expected for the diastereomeric phosphoramidite product, and only traces (less than 5%) of other phosphorous-containing contaminants. TLC of the product using the system described above showed one major species (>=95%) and two minor species of slightly lower mobility.

When 5'-N-trifluoroacetyl-5'-amino-5'-deoxythymidine is substituted for 5'-N-(9-fluorenylmethyloxycarbonyl)-5'-amino-5'-deoxythymidine, 5'-N-trifluoroacetyl-5'-amino-5'-deoxythymidine-3'-O-methyl-N, N-diisopropylamino phosphoramidite was obtained.

Similarly, the following compounds are prepared:

(1) 5'-N-(9-fluorenylmethyloxycarbonyl)-5'-amino-5'-deoxythymidine-3'-O-beta-cyanoethyl-N,N-diisopropylamino phosphoramidite.

(2) 5'-N-(9-fluorenylmethyloxycarbonyl)-5'-amino-5'-deoxythymidine-3'-O-methyl-N,N-dimethylamino phosphoramidite.

(3) 5'-N-(9-fluorenylmethyloxycarbonyl)-5'-amino-5'-deoxythymidine-3'-O-methylmorpholino phosphoramidite.

(4) 5'-N-(9-fluorenylmethyloxycarbonyl)-5'-amino-5'-deoxythymidine-3'-O-beta-cyanoethylmorpholino phosphoramidite.

(5) 5'-N-(9-fluorenylmethyloxycarbonyl)-5'-amino-5'-deoxythymidine-3'-O-p-nitrophenethyl-N,N-dimethylamino phosphoramidite.

(6) 5'-N-(9-fluorenylmethyloxycarbonyl)-5'-amino-5'-deoxythymidine-3'-O-betacyanoethyl-N,N-dimethylamino phosphoramidite.

(7) 5'-N-(9-fluorenylmethyloxycarbonyl)-5'-amino-2',5'-dideoxy-$N^6$-benzoyladenosine-3'-O-beta-cyanoethyl-N,N-diisopropylamino phosphoramidite.

(8) 5'-N-(9-fluorenylmethyloxycarbonyl)-5'-amino-2',5'-dideoxy-$N^2$-isobutyrylguanosine-3'-O-methyl-N,N-diisopropylamino phosphoramidite.

(9) 5'-N-(9-fluorenylmethyloxycarbonyl)-5'-amino-2',5'-dideoxy-$N^4$-benzoylcytidine-3'-O-methyl-N,N-dimethylamino phosphoramidite.

(10) 5'-N-(9-fluorenylmethyloxycarbonyl)-5'-amino-2',5'-dideoxyuridine-3'-O-methylmorpholino phosphoramidite.

(11) 5'-N-(9-fluorenylmethyloxycarbonyl)-5'-amino-2',5'-dideoxyinosine-3'-O-beta-cyanoethylmorpholino phosphoramidite.

(12) 5'-N-(9-fluorenylmethyloxycarbonyl)-5'-amino-2'-tetrahydropyranyl-5'-deoxyuridine-3'-O-p-nitrophenethyl-N,N-dimethylamino phosphoramidite.

(13) 5'-N-(9-fluorenylmethyloxycarbonyl)-5'-amino-2'-tetrahydropyranyl-5'-deoxyinosine-3'-O-beta-cyanoethyl-N,N-dimethylamino phosphoramidite.

EXAMPLE 6

5'-N-p-anisyldiphenylmethyl-5'-amino-5'-deoxythymidine-3'-O-beta-cyanoethyl-N,N-diisopropylamino phosphoramidite having the formula:

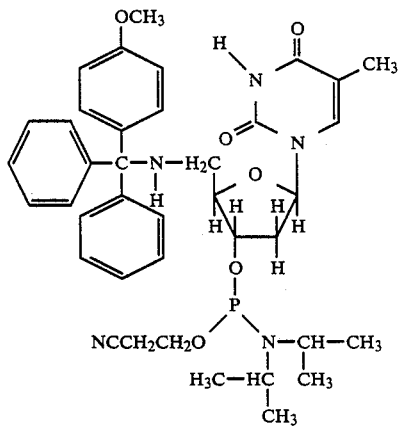

5'-N-p-anisyldiphenylmethyl-5'-amino-5'-deoxythymidine (0.785 g, 1.5 mmole) was dissolved in dry dichloromethane (10 ml, dried by distillation from phosphorous pentoxide and then calcium hydride) containing N,N-diisopropylethylamine (1.3 ml) under a dry argon atmosphere. Chloro-N,N-diisopropylamino-beta-cyanoethoxyphosphine (0.70 ml, 3.0 mmole) was added dropwise to the solution from a syringe over about one minute and the reaction stirred at room temperature. TLC on silica gel 60 F-254 plates developed in ethyl acetate: triethylamine (99:1 v/v) indicated that the reaction was complete after thirty minutes. Anhydrous methanol (0.1 ml) was then added to decompose excess phosphitylating agent, and the reaction stirred a few minutes longer. The reaction mixture was then transferred to a separatory funnel with ethyl acetate (50 ml, previously washed with 50 ml of cold 10% (w/v) aqueous sodium carbonate) and washed twice with cold 10% (w/v) aqueous sodium carbonate (80 ml portions) and twice with cold saturated aqueous sodium chloride (80 ml portions). The organic solution was then dried over anhydrous sodium sulfate, filtered, and rotary evaporated under reduced pressure to a clear foam. The foam was dissolved in dry ethyl acetate (10–15 ml) and this solution was added dropwise to hexane (200 ml) at −78° C. (dry ice/acetone bath). The precipitated product was filtered, washed well with −78° hexane, and dried in a vacuum dessicator to yield 0.932 g (1.31 mmoles, 87%) of a white powdery solid. The structure of the product was further confirmed by $^1$H NMR spectroscopy in perdeuterated acetonitrile. $^{31}$P NMR spectroscopy in perdeuterated acetonitrile showed two singlets at 147.74 and 147.53 ppm (relative to phosphoric acid in perdeuterated acetonitrile) as expected for the diastereomeric phosphoramidite product, and only traces (<5%) of other phosphorous-containing impurities. TLC in the above solvent system on silica gel LQ6DF plates showed two closely migrating spots under short wave UV detection, $R_f$ 0.87 and 0.92, once again due to the diastereomeric product. These spots gave an yellow-orange color characteristic of the p-anisyldiphenylmethyl cation when exposed to perchloric acid:ethanol solution (3:2 v/v).

When the foregoing Example was repeated using chloro-N,N-diisopropylaminomethoxyphosphine in lieu of chloro-N,N-diisopropylamino-beta-cyanoethoxyphosphine, 5'-N-p-anisyldiphenylmethyl-5'-amino-5'-deoxythymidine-3'-O-methyl-N,N-diisopropylamino phosphoramidite was obtained.

Similarly, the following compounds are prepared:
(1) 5'-N-p-anisyldiphenylmethyl-5'-amino-5'-deoxythymidine-3'-O-methyl-N,N-diisopropylamino phosphoramidite.
(2) 5'-N-p-anisyldiphenylmethyl-5'-amino-5'-deoxythymidine-3'-O-methyl-N,N-dimethylamino phosphoramidite.
(3) 5'-N-p-anisyldiphenylmethyl-5'-amino-5'-deoxythymidine-3'-O-methylmorpholino phosphoramidite.
(4) 5'-N-p-anisyldiphenylmethyl-5'-amino-5'-deoxythymidine-3'-O-beta-cyanoethylmorpholino phosphoramidite.
(5) 5'-N-p-anisyldiphenylmethyl-5'-amino-5'-deoxythymidine-3'-O-p-nitrophenethyl-N,N-dimethylamino phosphoramidite.
(6) 5'-N-p-anisyldiphenylmethyl-5'-amino-5'-deoxythymidine-3'-O-betacyanoethyl-N,N-dimethylamino phosphoramidite.
(7) 5'-N-p-anisyldiphenylmethyl 5'-amino-2',5'-dideoxyuridine-3'-O-beta-cyanoethyl-N,N-diisopropylamino phosphoramidite.
(8) 5'-N-p-anisyldiphenylmethyl 5'-amino-2',5'-dideoxyinosine-3'-O-methyl-N,N-diisopropylamino phosphoramidite.
(9) 5'-N-p-anisyldiphenylmethyl 5'-amino-N$^6$-benzoyl-2',5'-dideoxyadenosine-3'-O-methyl-N,N-dimethylamino phosphoramidite.
(10) 5'-N-p-anisyldiphenylmethyl 5'-amino-N$^4$-benzoyl-2',5'-dideoxycytosine-3'-O-methylmorpholino phosphoramidite.
(11) 5'-N-p-anisyldiphenylmethyl 5'-amino-N$^2$-isobutyryl-2',5'-dideoxyguanosine-3'-O-beta-cyanoethylmorpholino phosphoramidite.
(12) 5'-N-p-anisyldiphenylmethyl 5'-amino-2'-tetrahydropyranyl-5'-deoxyuridine-3'-O-p-nitrophenethyl-N,N-dimethylamino phosphoramidite.
(13) syldiphenylmethyl 5'-amino-2'-tetrahydropyranyl-5'-deoxyinosine-3'-O-beta-cyanoethyl-N,N-dimethyl amino phosphoramidite.
(14) 5'-N-p-anisyldiphenylmethyl 5'-amino-2'-tetrahydropyranyl-N$^6$-benzoyl-5'-deoxyadenosine-3'-O-beta-cyanoethyl-N,N-diisopropylamino phosphoramidite.
(15) 5'-N-p-anisyldiphenylmethyl 5'-amino-2'-tetrahydropyranyl-N$^4$-benzoyl-5'-deoxycytosine-3'-O-methyl-N,N-diisopropylamino phosphoramidite.
(16) 5'-N-p-anisyldiphenylmethyl 5'-amino-2'-tetrahydropyranyl-N$^2$-isobutyryl-5'-deoxyguanosine-3'-O-methyl-N,N-dimethylamino phosphoramidite.

Composition of Matter No. 3: 2'-N-protected derivatives of 5'-O-protected 2'-amino-2'-deoxyuridine and 5'-O-protected 2'-N-aminoacyl-2'-amino-2'-deoxyuridine, a preferred class of compounds within the scope of FIG. 5, having the generic formula:

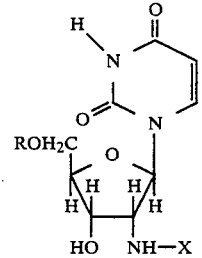

wherein R = triphenylmethyl (trityl), p-anisyldiphenylmethyl (monomethoxytrityl, MMT), di-p-anisylphenylmethyl (dimethoxytrityl, DMT), 9-phenylxanthenyl (pixyl), di-o-anisyl-1-napthylmethyl, p-anisyl-1-napthylphenylmethyl, or the like;

wherein X = a standard nitrogen protecting group as defined in the generic description of the invention accompanying FIG. 5; preferably, X = trifluoroacetyl (Tfa), 9-fluorenylmethyloxycarbonyl (Fmoc), triphenylmethyl (trityl), or p-anisyldiphenylmethyl (also referred to as monomethoxytrityl, MMT).

The formula also encompasses a related class of compounds formed by reacting the compound wherein X = H with an activated appropriately protected amino acid derivative; in this case, X is represente by X = Y—NH—(CHQ)$_n$—CO, wherein Y = a standard nitrogen protecting group as defined for X hereinabove, especially those listed as preferable for X hereinabove; and Q = any common amino acid side chain, with n = 1 to about 12, generally n <= 6; for n = 1, Q includes, but is not limited to, such moieties as H (from the amino acid glycine), methyl (from the amino acid alanine), isopropyl (valine), benzyl (phenylalanine), p-hydroxybenzyl (tyrosine), carboxymethyl (aspartic acid), carboxyethyl (glutamic acid), 4-aminobutyl (lysine), imidazolylmethyl (histidine), indolylmethyl (tryptophan), mercaptomethyl (cystine), or hydroxymethyl (serine); for $n>1$, Q is generally H: for example, when $n=2$, the corresponding amino acid is beta-alanine; when $n=3$, 4-aminobutyric acid; when $n=5$, 6-aminohexanoic acid. If Q contains reactive moieties such as OH, SH, $CO_2H$, or $NH_2$, these are also appropriately protected with standard groups (see Geiger and Konig, "The Peptides: Analysis, Synthesis, Biology", for a thorough description of such groups). In this class of compounds, the protected amino group is spatially removed from the sugar ring of the nucleoside, either to improve its reactivity or to spatially separate the DNA chain from the "tag" that is to be affixed to the amino group.

The formula also encompasses a class of compounds related to this latter class by having more than one amino acid linked in linear fashion (termed a peptide) attached to the compound wherein $X=H$; in this case, X is represented by $X=Y-[NH-(CHQ_i)_n-CO]_m$, wherein Y and n are as defined hereinabove, the various $Q_i$ are as defined for Q hereinabove, with $i=1$ to the maximum value of m, and $m=1$ to about 100; $m=1$ represents the class defined in the paragraph above.

EXAMPLES

The syntheses of the starting compounds 2'-azido-2'-deoxyuridine, 2'-amino-2'-deoxyuridine, 2'-N-(N-benzyloxycarbonylglycyl)-2'-amino-2'-deoxyuridine, 2'-N-glycyl-2'-amino-2'-deoxyuridine, and 2'-trifluoroacetamido-2'-deoxyuridine are given in:

Verheyden, J. P. H., Wagener, D., and Moffatt, J. G., *J. Org. Chem.* 36, 250-254 (1971).

Sharma, R. A., Bobek, M., and Bloch, A., *J. Med. Chem.* 18, 955-957 (1975).

Imazawa, M., and Eckstein, F., *J. Org. Chem.* 44, 2039-2041 (1979).

Generally, the procedures found therein were followed with only minor modifications to the workups, except:

(1) 2'-azido-2'-deoxyuridine was purified on a column of neutral alumina in methanol:acetone (1:1 v/v) instead of on silica gel;

(2) 2'-amino-2'-deoxyuridine was obtained by reduction of 2'-azido-2'-deoxyuridine with hydrogen in the presence of 5% palladium on carbon catalyst, instead of using triphenylphosphine and ammonia;

(3) N-trifluoroacetylation of 2'-amino-2'-deoxyuridine was carried out using p-nitrophenyl trifluoroacetate followed by column chromatography on silica gel in chloroform:methanol (6:1 v/v), instead of using S-ethylthioltrifluoroacetate.

EXAMPLE 7

5'-O-di-p-anisylphenylmethyl-2'-N-trifluoroacetyl-2'-amino-2'-deoxyuridine having the formula:

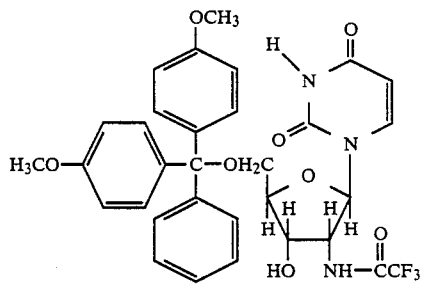

2'-N-trifluoroacetyl-2'-amino-2'-deoxyuridine (1.25 g, 3.8 mmoles) was dissolved in anhydrous pyridine (50 ml), and di-p-anisylphenylmethyl chloride (1.42 g, 4.2 mmoles; American Bionuclear Corporation) was added. The orange solution was then stirred overnight at room temperature in the dark. Water (10 ml) was added, and the mixture stirred an additional hour. The solvent was removed by rotary evaporation at 40° C. to give a resinous product, which was co-evaporated twice with toluene (100 ml portions). The foamy product was partitioned between water (50 ml) and ethyl acetate (100 ml), the layers separated, and the organic layer extracted with water (50 ml) and saturated aqueous sodium chloride (50 ml). The ethyl acetate solution was dried over anhydrous sodium sulfate, filtered, and evaporated to a yellow foam. This foam was then dissolved in an minimum volume of ethyl acetate:triethylamine (9:1 v/v), and applied to a column of silica gel (3 cm×25 cm) poured in the same solvent mixture. The column was eluted with ethyl acetate:triethylamine (9:1 v/v); fractions containing product were pooled and evaporated to a clear glassy solid. The product was dissolved in a minimum volume of ethyl acetate (about 10 ml) and precipitated into hexane (200 ml) at room temperature. The gelatinous precipitate was filtered and dried in a vacuum dessicator to give 2.06 g (3.3 mmoles, 86%) of a white power, not crystallized. TLC analysis of the purified product on silic gel 60 F-254 plates developed in chloroform: ethanol (9:1 v/v) showed one spot by short wave UV detection, $R_f$ 0.60, that gave a bright orange color characteristic of the di-p-anisylphenylmethyl cation after spraying the plate with perchloric acid:ethanol solution (3:2 v/v). The structure of the product was further confirmed by $^1H$ NMR spectroscopy in perdeuterated dimethyl sulfoxide. Fluorine ($^{19}F$) NMR spectroscopy in deuterated chloroform (Aldrich Chemical Company) showed one singlet at 6.03 ppm (relative to trifluoracetic acid in deuterated chloroform) as expected for the single trifluoroacetyl group.

Similarly, the following compounds are prepared:

(1) 5'-O-di-p-anisylphenylmethyl-2'-N-trifluoroacetyl-2'-amino-2'-deoxyinosine.

(2) 5'-O-di-p-anisylphenylmethyl-2'-N-trifluoroacetyl-2'-amino-$N^6$-benzoyl-2'-deoxyadenosine.

(3) 5'-O-di-p-anisylphenylmethyl-2'-N-trifluoroacetyl-2'-amino-$N^4$-benzoyl-2'-deoxycytosine.

(4) 5'-O-di-p-anisylphenylmethyl-2'-N-trifluoroacetyl-2'-amino-$N^2$-isobutyryl-2'-deoxyguanosine.

(5) 5'-O-di-p-anisylphenylmethyl-2'-N-(9-fluorenylmethyloxycarbonyl)-2'-amino-2'-deoxyinosine.

(6) 5'-O-di-p-anisylphenylmethyl-2'-N-(9-fluorenylmethyloxycarbonyl)-2'-amino-$N^6$-benzoyl-2'-deoxyadenosine.

(7) 5'-O-di-p-anisylphenylmethyl-2'-N-(9-fluorenylmethyloxycarbonyl-2'-amino-N$^4$-benzoyl-2'-deoxycytosine.
(8) 5'-O-di-p-anisylphenylmethyl-2'-N-(9-fluorenylmethyloxycarbonyl-2'-amino-N$^2$-isobutyryl-2'-deoxyguanosine.
(9) 5'-O-di-p-anisylphenylmethyl-2'-N-(9-fluorenylmethyloxycarbonyl)-2'-amino-2'-deoxyuridine.

EXAMPLE 8

5'-O-di-p-anisylphenylmethyl-2'-N-(N-trifluoroacetylglycyl)-2'-amino-2'-deoxyuridine having the formula:

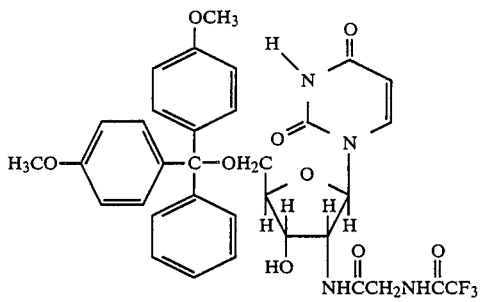

2'-N-glycyl-2'-amino-2'-deoxyuridine (1.2 g, 4.0 mmole) and p-nitrophenyl trifluoroacetate (1.2 g, 5.1 mmole; Aldrich Chemical Company) were dissolved in anhydrous DMF (20 ml) and the mixture was stirred overnight at room temperature. The reaction mixture was then rotary evaporated to dryness at 50° C., and the gummy yellow residue flash chromatographed (see Still, W. C., Kahn, M., and Mitra, A., *J. Org. Chem.* 43, 2923–2925 (1978)) on a column of silica gel 60 (2.5 cm × 10 inches) in ethyl acetate:methanol (95:5 v/v). Fractions containing product were evaporated to dryness to give a white foam (1.5 g, 3.7 mmoles, 93%) which was not crystallized, but used directly in the next step.

The above material (1.5 g, 3.7 mmoles) was evaporated twice with dry pyridine (30 ml portions), and the residue dissolved in dry pyridine (50 ml). N,N-dimethylaminopyridine (23 mg, 0.19 mmoles), triethylamine (0.8 ml, 5.2 mmoles), and di-p-anisylphenylmethyl chloride (1.54 g, 4.4 mmoles) were added, and the orange mixture stirred overnight at room temperature. Aqueous sodium bicarbonate (5% w/v, 50 ml) was then added, and the mixture stirred fifteen minutes more. The mixture was extracted twice with ethyl acetate (100 ml portions), and the combined ethyl acetate layers washed once with saturated aqueous sodium chloride (50 ml), dried over anhydrous sodium sulfate, filtered, and evaporated to dryness. After two co-evaporations with toluene (100 ml portions), the foamy yellow product was purified by chromatography on a column (3 cm × 25 cm) of silica gel 60 using chloroform:methanol:triethylamine (89:10:1 v/v) as the eluant. Fractions containing product were pooled and evaporated to dryness to give a clear glassy solid. This material was dissolved in a minimum of ethyl acetate (about 10 ml) and precipitated into hexane (300 ml) at room temperatuare. The product was filtered and dried in a vacuum dessicator to give 1.62 g (2.3 mmoles, 62%) of a powdery white solid, which could be crystallized from benzene/hexane. TLC analysis of the purified product on silica gel 60 F-254 plates developed in dichloromethane:methanol (92:8 v/v) showed one spot by short wave UV detection, R$_f$ 0.33, that gave a bright orange color characteristic of the di-p-anisylphenylmethyl cation after spraying the plate with perchloric acid:ethanol solution (3:2 v/v). The structure of the product was further confirmed by $^1$H NMR spectroscopy in perdeuterated dimethyl sulfoxide. $^{19}$F NMR spectroscopy in deuterated chloroform showed one singlet at 5.98 ppm (relative to trifluoroacetic acid in deuterated chloroform) as expected for the single trifluoroacetyl group.

Similarly, the following compounds are prepared:
(1) 5'-O-di-p-anisylphenylmethyl-2'-N-(N-trifluoroacetylglycyl)-2'-amino-N$^2$-isobutyryl-2'-deoxyguanosine.
(2) 5'-O-di-p-anisylphenylmethyl-2'-N-(N-trifluoroacetylglycyl)-2'-amino-2'-deoxyinosine.
(3) 5'-O-di-p-anisylphenylmethyl-2'-N-(N-trifluoroacetylglycyl)-2'-amino-N$^6$-benzoyl-2'-deoxyadenosine.
(4) 5'-O-di-p-anisylphenylmethyl-2'-N-(N-trifluoroacetylglycyl)-2'-amino-N$^4$-benzoyl-2'-deoxycytosine.
(5) 5'-O-di-p-anisylphenylmethyl-2'-N-(N-9-fluorenylmethyloxycarbonyl-glycyl)-2'-amino-N$^2$-isobutyryl-2'-deoxyguanosine.
(6) 5'-O-di-p-anisylphenylmethyl-2'-N-(N-9-fluorenylmethyloxycarbonyl-glycyl)-2'-amino-2'-deoxyuridine.
(7) 5'-O-di-p-anisylphenylmethyl-2'-N-(N-9-fluorenylmethyloxycarbonyl-glycyl)-2'-amino-2'-deoxyinosine.
(8) 5'-O-di-p-anisylphenylmethyl-2'-N-(N-9-fluorenylmethyloxycarbonyl-glycyl)-2'-amino-N$^6$-benzoyl-2'-deoxyadenosine.
(9) 5'-O-di-p-anisylphenylmethyl-2'-N-(N-9-fluorenylmethyloxycarbonyl-glycyl)-2'-amino-N$^4$-benzoyl-2'-deoxycytosine.

Composition of Matter No. 4:

3'-O-phosphoramidites of compounds described in composition of matter No. 3 having the generic formula:

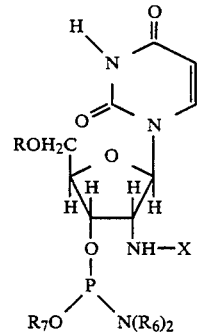

wherein R = as defined in the previous section (composition of matter No. 3);
X = as defined in the previous section (composition of matter No. 3);
R$_6$ = a lower alkyl, preferably a lower alkyl such as methyl or isopropyl, or a non-aromatic nitrogen-containing heterocycle, such as morpholino, piperidino, pyrrolidino, or 2,2,6,6-tetramethylpiperidono,
R$_7$ = methyl, beta-cyanoethyl, p-nitrophenethyl, o-chlorophenyl, or p-chlorophenyl.

EXAMPLES

NOTE: The procedures described in this section are essentially the same as those described in the section entitled "Composition of Matter No. 2". The phosphine starting material used to synthesize the following phosphoramidite compounds were prepared according to the literature references given in that section.

EXAMPLE 9

5'-O-di-p-anisylphenylmethyl-2'-N-trifluoroacetyl-2'-amino-2'-deoxyuridine-3'-O-methyl-N,N-diisopropylamino phosphoramidite having the formula:

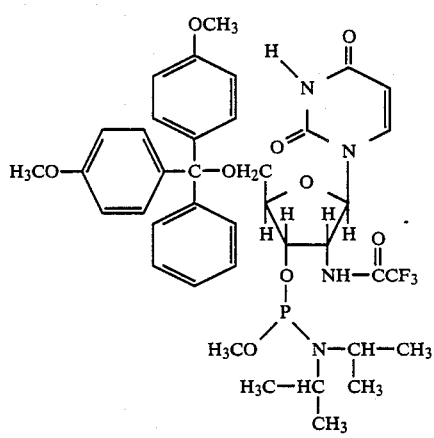

5'-O-di-p-anisylphenylmethyl-2'-N-trifluoroacetyl-2'-amino-2'-deoxyuridine (0.95 g, 1.5 mmoles) was dissolved in dry dichloromethane (10 ml, dried by distillation from phosphorous pentoxide and then calcium hydride) containing N,N-diisopropylethylamine (1.3 ml, 5.0 mmoles). The solution was stirred at room temperature under a dry argon atmosphere, and chloro-N,N-diisopropylaminomethoxyphosphine (0.45 ml, 2.4 mmoles) was added dropwise from a syringe over about one minute. TLC on silica gel 60 F-254 plates developed in ethyl acetate:triethylamine (99:1 v/v) indicated that the reaction was complete after thirty minutes. Anhydrous methanol (0.1 ml) was then added to decompose excess phosphitylating agent, and the reaction stirred a few minutes longer. The reaction mixture was then transferred to a separatory funnel with ethyl acetate (50 ml, previously washed with 50 ml of cold 10% (w/v) aqueous sodium carbonate) and washed twice with cold 10% (w/v) aqueous sodium carbonate (80 ml portions), and twice with cold saturated aqueous sodium chloride (80 ml portions). The organic solution was dried over anhydrous sodium sulfate, filtered, and rotary evaporated under reduced pressure to a clear foam. The foam was dissolved in dry ethyl acetate (10–15 ml) and this solution was added dropwise to hexane (200 ml) at −78° C. (dry ice-acetone bath). The precipitated product was filtered, washed well with −78° C. hexane, and dried in a vacuum dessicator to yield 1.04 g (1.3 mmoles, 87%) of a white powdery solid. The structure of the product was confirmed by $^1$H NMR spectroscopy in perdeuterated acetonitrile. $^{31}$P NMR spectroscopy in perdeuterated acetonitrile showed two singlets at 152.11 and 150.43 ppm (relative to phosphoric acid in perdeuterated acetonitrile) as expected for the diastereomeric phosphoramidite product, and only very slight traces (<1%) of other phosphorus-containing impurities. $^{19}$F NMR spectroscopy in deuterated chloroform also showed two singlets at 0.42 and 0.38 ppm (relative to trifluoroacetic acid in deuterated chloroform), due to a slight influence of the neighboring chiral phosphorous. TLC in the above solvent system on silica gel LQ6DF plates showed only one spot under short wave UV detection, $R_f$ 0.96. This spot gave a bright orange color characteristic of the di-p-anisylphenylmethyl cation when exposed to perchloric acid:ethanol (3:2 v/v).

Similarly, the following compounds are prepared:
(1) 5'-O-di-p-anisylphenylmethyl-2'-N-trifluoroacetyl-2'-amino-2'-deoxyuridine-3'-O-beta-cyanoethyl-N,N-diisopropylamino phosphoramidite.
(2) 5'-O-di-p-anisylphenylmethyl-2'-N-trifluoroacetyl2'-amino-2'-deoxyuridine-3'-O-methyl-N,N-dimethylamino phosphoramidite.
(3) 5'-O-di-p-anisylphenylmethyl-2'-N-trifluoroacetyl-2'-amino-2'-deoxyuridine-3'-O-methyl-morpholino phosphoramidite.
(4) 5'-O-di-p-anisylphenylmethyl-2'-N-trifluoroacetyl2'-amino-2'-deoxyuridine-3'-O-beta-cyanoethyl-morpholino phosphoramidite.
(5) 5'-O-di-p-anisylphenylmethyl-2'-N-trifluoroacetyl-2'-amino-2'-deoxyuridine-3'-O-p-nitrophenethyl-N,N-dimethylamino phosphoramidite.
(6) 5'-O-di-p-anisylphenylmethyl-2'-N-trifluoroacetyl-2'-amino-2'-deoxyuridine-3'-O-beta-cyanoethyl-N,N-dimethylamino phosphoramidite.
(7) 5'-O-di-p-anisylphenylmethyl-2'-N-trifluoroacetyl-2'-amino-2'-deoxyinosine-3'-O-methyl-N,N-diisopropylamino phosphoramidite.
(8) 5'-O-di-p-anisylphenylmethyl-2'-N-trifluoroacetyl-2'-amino-N$^6$-benzoyl-2'-deoxyadenosine-3'-O-methyl-N,N-dimethylamino phosphoramidite.
(9) 5'-O-di-p-anisylphenylmethyl-2'-N-trifluoroacetyl-2'-amino-N$^4$-benzoyl-2'-deoxycytosine-3'-O-methyl-morpholino phosphoramidite.
(10) 5'-O-di-p-anisylphenylmethyl-2'-N-trifluoroacetyl-2'-amino-N$^2$-isobutyryl-2'-deoxyguanosine-3'-O-beta-cyanoethylmorpholino phosphoramidite.
(11) 5'-O-di-p-anisylphenylmethyl-2'-N-trifluoroacetyl-2'-amino-2'-deoxyinosine-3'-O-betacyanoethyl-N,N-dimethylamino phosphoramidite.
(12) 5'-O-di-p-anisylphenylmethyl-2'N-(-9-fluorenylmethyloxycarbonyl)-2'-amino-2'-deoxyuridine-3'-O-beta-cyanoethyl-N,N-diisopropylamino phosphoramidite.
(13) 5'-O-di-p-anisylphenylmethyl-2'N-(-9-fluorenylmethyloxycarbonyl)-2'-amino-2'-deoxyuridine-3'-O-methyl-N,N-diisopropylamino phosphoramidite.
(14) 5'-O-di-p-anisylphenylmethyl-2'N-(-9-fluorenylmethyloxycarbonyl)-2'-amino-2'-deoxyuridine-3'-O-methyl-N,N-dimethylamino phosphoramidite.
(15) 5'-O-di-p-anisylphenylmethyl-2'N-(-9-fluorenylmethyloxycarbonyl)-2'-amino-2'-deoxyuridine-3'-O-methylmorpholino phosphoramidite.
(16) 5'-O-di-p-anisylphenylmethyl-2'N-(-9-fluorenylmethyloxycarbonyl)-2'-amino-2'-deoxyuridine-3'-O-beta-cyanoethylmorpholino phosphoramidite.
(17) 5'-O-di-p-anisylphenylmethyl-2'N-(-9-fluorenylmethyloxycarbonyl)-2'-amino-2'-deoxyuridine-3'-O-p-nitrophenethyl-N,N-dimethylamino phosphoramidite.
(18) 5'-O-di-p-anisylphenylmethyl-2'N-(-9-fluorenylmethyloxycarbonyl)-2'-amino-2'-deoxyuridine-3'-O-beta-cyanoethyl-N,N-dimethylamino phosphoramidite.

(19) 5'-O-di-p-anisylphenylmethyl-2'N-(-9-fluorenylmethyloxycarbonyl)-2'-amino-2'-deoxyinosine-3'-O-methyl-N,N-diisopropylamino phosphoramidite.
(20) 5'-O-di-p-anisylphenylmethyl-2'N-(-9-fluorenylmethyloxycarbonyl)-2'-amino-N6-benzoyl-2'-deoxyadenosine-3'-O-methyl-N,N-dimethylamino phosphoramidite.
(21) 5'-O-di-p-anisylphenylmethyl-2'N-(-9-fluorenylmethyloxycarbonyl)-2'-amino-N4-benzoyl-2'-deoxycytosine-3'-O-methylmorpholino phosphoramidite.
(22) 5'-O-di-p-anisylphenylmethyl-2'N-(-9-fluorenylmethyloxycarbonyl)-2'-amino-N2-isobutyryl-2'-deoxyguanosine-3'O-beta-cyanoethyl morpholino phosphoramidite.
(23) 5'-O-di-p-anisylphenylmethyl-2'N-(-9-fluorenylmethyloxycarbonyl)-2'-amino-2'-deoxyinosine-3'-O-beta-cyanoethyl-N,N-dimethylamino phosphoramidite.

EXAMPLE 10

5'-O-di-p-anisylphenylmethyl-2'-N-(N-trifluoroacetylglycyl)-2'-amino-2'-deoxyuridine-3'-O-methyl-N,N-diisopropylamino phosphoramidite having the formula:

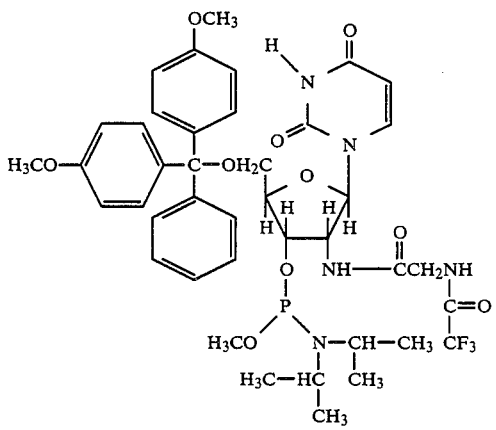

5'-O-di-p-anisylphenylmethyl-2'-N-(N-trifluoroacetyl-glycyl)-2'-amino-2'-deoxyuridine (1.07 g, 1.5 mmoles) was dissolved in dry dichloromethane (10 ml, dried by distillation from phosphorous pentoxide and then calcium hydride) containing N,N-diisopropylethylamine (1.3 ml, 5.0 mmoles). The solution was stirred at room temperature under a dry argon atmosphere, and chloro-N,N-diisopropylaminomethoxyphosphine (0.45 ml, 2.4 mmoles) was added dropwise from a syringe over about one minute. TLC on silica gel 60 F-254 plates developed in ethyl acetate:triethylamine (99:1 v/v) indicated that the reaction was complete after thirty minutes. Anhydrous methanol (0.1 ml) was added to decompose excess phosphitylating agent, and the reaction stirred a few minutes longer. The reaction mixture was then transferred to a separatory funnel with ethyl acetate (50 ml, previously washed with 50 ml of cold 10% (w/v) aqueous sodium carbonate) and washed twice with cold 10% (w/v) aqueous sodium carbonate (80 ml portions), and twice with cold saturated aqueous sodium chloride (80 ml portions). The organic solution was dried over anhydrous sodium sulfate, filtered, and rotary evaporated under reduced pressure to a clear foam. The foam was dissolved in dry ethyl acetate (10–15 ml) and this solution was added dropwise to hexane (200 ml) at −78° C. (dry ice-acetone bath). The precipitated product was filtered, washed well with −78° C. hexane, and dried in a vacuum desiccator to yield 1.23 g (1.4 mmoles, 93%) of a white powdery solid. The structure of the product was confirmed by $^1$H NMR spectroscopy in perdeuterated acetonitrile. $^{31}$P NMR spectroscopy in perdeuterated acetonitrile showed two singlets at 151.25 and 148.96 ppm (relative to phosphoric acid in perdeuterated acetonitrile) as expected for the diastereomeric phosphoramidite product, and only very slight traces (<2%) of other phosphorous containing impurities. $^{19}$F NMR spectroscopy in deuterated chloroform showed one singlet at 0.66 ppm (relative to trifluoroacetic acid in deuterated chloroform). TLC in the above solvent system on silica gel LQ6DF plates showed only one spot under short wave UV detection, $R_f$0.91. This spot gave a bright orange color characteristic of the di-p-anisylphenylmethyl cation when exposed to perchloric acid:ethanol (3:2 v/v).

Similarly, the following compounds are prepared:
(1) 5'-O-di-p-anisylphenylmethyl-2'-N-(N-trifluoroacetylglycyl)-2'-amino-2'-deoxyuridine-3'-O-beta-cyanoethyl-N,N-diisopropylamino phosphoramidite.
(2) 5'-O-di-p-anisylphenylmethyl-2'-N-(N-trifluoroacetylglycyl)-2'-amino-2'-deoxyuridine-3'-O-methyl-N,N-dimethylamino phosphoramidite.
(3) 5'-O-di-p-anisylphenylmethyl-2'-N-(N-trifluoroacetylglycyl)-2'-amino-2'-deoxyuridine-3'-O-methyl-morpholino phosphoramidite.
(4) 5'-O-di-p-anisylphenylmethyl-2'-N-(N-trifluoroacetylglycyl)-2'-amino-2'-deoxyuridine-3'-O-beta-cyanoethylmorpholino phosphoramidite.
(5) 5'-O-di-p-anisylphenylmethyl-2'-N-(N-trifluoroacetylglycyl)-2'-amino-2'-deoxyuridine-3'-O-p-nitrophenethyl-N,N-dimethylamino phosphoramidite.
(6) 5'-O-di-p-anisylphenylmethyl-2'-N-(N-trifluoroacetylglycyl)-2"-amino-2'-deoxyuridine-3'-O-betacyanoethyl-N,N-dimethylamino phosphoramidite.
(7) 5'-O-di-p-anisylphenylmethyl-2'-N-(N-trifluoroacetylglycyl)-2'-amino-2'-deoxyinosine-3'-O-methyl-N,N-diisopropylamino phosphoramidite.
(8) 5'-O-di-p-anisylphenylmethyl-2'-N-(N-trifluoroacetylglycyl)-2'-amino-N6-benzoyl-2'-deoxyadenosine-3'-O-methyl-N,N-dimethylamino phosphoramidite.
(9) 5'-O-di-p-anisylphenylmethyl-2'-N-(N-trifluoroacetylglycyl)-2'-amino-N4-benzoyl-2'-deoxycytosine-3'-O-methylmorpholino phosphoramidite.
(10) 5'-O-di-p-anisylphenylmethyl-2'-N-(N-trifluoroacetylglycyl)-2'-amino-2'-deoxyinosine-3'-O-beta-cyanoethyl-N,N-dimethylamino phosphoramidite.
(11) 5'-O-di-p-anisylphenylmethyl-2'-N-(N-trifluoroacetylglycyl)-2'-amino-N6-benzoyl-2'-deoxyadenosine-3'-O-p-nitrophenethyl-N,N-dimethylamino phosphoramidite.
(12) 5'-O-di-p-anisylphenylmethyl-2'-N-(N-trifluoroacetylglycyl)-2'-amino-N4-benzoyl-2'-deoxycytosine-3'-O-betacyanoethyl morpholino phosphoramidite.
(13) 5'-O-di-p-anisylphenylmethyl-2'-N-(N-9-fluorenylmethyloxycarbonylglycyl)-2'-amino-2'-deoxyuridine-3'-O-beta-cyanoethyl-N,N-dimethylamino phosphoramidite.

(14) 5'-O-di-p-anisylphenylmethyl-2'-N-(N-9-fluorenylmethyloxycarbonylglycyl)-2'-amino-2'-deoxyinosine-3'-O-beta-cyanoethyl-N,N-dimethylamino phosphoramidite.

(15) 5'-O-di-p-anisylphenylmethyl-2'-N-(N-9-fluorenylmethyloxycarbonylglycyl)-2'-amino-$N^6$-benzoyl-2'-deoxyadenosine 3'-O-p-nitrophenethyl-N,N-dimethylamino phosphoramidite.

(16) 5'-O-di-p-anisylphenylmethyl-2'-N-(N-9-fluorenylmethyloxycarbonylglycyl)-2'-amino-$N^4$-benzoyl-2'-deoxycytosine-3'-O-beta-cyanoethyl-morpholino phosphoramidite.

USES OF THE INVENTION (1) Synthesis of oligodeoxyribonucleotides containing a 5'-amino terminus The steps involved in the use of protected 5'-aminonucleoside phosphoramidites for the synthesis of oligodeoxyribonucleotides containing a 5'-amino terminus are shown in the Figure of Example 11, and are described in the following text.

The protected 5'-amino-nucleoside-3'-O-phosphoramidites, preferably those in which $B_n$=thymine, X=Fmoc or MMT, $R_6$=isopropyl, and $R_7$=methyl or beta-cyanoethyl, most preferably beta-cyanoethyl, are coupled to the 5'-hydroxyl of a growing oligodeoxyribonucleotide attached to a solid support using standard phosphoramidite DNA synthesis techniques (see Atkinson, T., and Smith, M., in "Oligonucleotide Synthesis: A Practical Approach," Gait, M. J., pp. 35–82, IRL Press, Oxford, England (1984) and the references cited therein). Briefly, this procedure consists of reacting a protected 5'-amino-nucleoside 3'-O-phosphoramidite in anhydrous acetonitrile solution with the support-bound oligonucleotide in the presence of 1H-tetrazole under inert atmosphere, washing away excess reactants from product on the support, and then oxidizing the phosphite product to the desired phosphate with a solution of iodine in basic aqueous tetrahydrofuran. Generally, a ten-to-twenty-fold excess of phosphoramidite and a fifty-to-one hundredfold excess of tetrazole over support-bound oligonucleotide are used; for the synthesis using the protected 5'-amino phosphoramidites, a twenty-fold excess of phosphoramidite and a one hundred-fold excess of tetrazole are preferred. Under these conditibns, both the Fmoc-protected (Example 5) and the MMT-protected (Example 6) phosphoramidites routinely couple in better than 90% yield, generally in better than 95% yield. The couplings can be performed manually utilizing a six minute coupling reaction time and a three minute oxidation reaction time, or on an Applied Biosystems Model 380A automated DNA synthesizer (or similar instrument designed to accomodate the phosphoramidite chemistry) utilizing the accompanying pre-programmed synthesis cycles.

The 5'-amino oligonucleotide is then obtained by cleaving the DNA from the support by treatment for at least four hours with concentrated ammonium hydroxide solution at room temperature, followed by deprotection of the DNA bases in the same solution at 55° C. for twelve to sixteen hours. When $R_7$=methyl, a treatment with triethylammonium thiophenoxide in dioxane for one hour at room temperature is also required prior to cleavage of the DNA from the support.

When X=Fmoc, the ammonium hydroxide treatments further serve to remove the base-labile Fmoc amino-protecting group and to yield an oligonucleotide product with a free 5'-amino terminus. The DNA-containing ammonium hydroxide solution is then lyophilized to dryness. This material can be further purified either by reverse phase high performance liquid chromatography (RP HPLC) on an octadecylsilyl silica ($C_{18}$) column utilizing an increasing acetonitrile gradient in triethylammonium acetate buffer at near neutral pH (6.5–7.0), or by preparative polyacrylamide gel electrophoresis, a somewhat longer and more laborious procedure. For long oligonucleotides (>20 nucleotide subunits) the RP HPLC purification is generally unsatisfactory for the free 5'-amino DNA, due both to the increase in the amount of failure sequences (that is, a decreased overall yield of correct sequence DNA due to the large number of couplings) to be separated from the desired product, and the reduction in the resolving power of the $C_{18}$ column for long DNA sequences.

When X=MMT, the cleavage and deprotection treatments in ammonium hydroxide do not affect the base-stable, acid-labile MMT amino-protecting group. Thus, the desired product retains the MMT moiety on the 5'-amino group. This MMT group imparts an increased hydrophobicity to the desired product DNA, resulting in a marked increase in retention time during RP HPLC on a $C_{18}$ column. The contaminating failure DNA sequences elute from the column much earlier than the desired oligonucleotide, which subsequently elutes in a clean and well-resolved fashion. The MMT protecting group can then be removed by mild acid treatment with acetic acid/water (80:20 v/v) solution at room temperature for twenty to thirty minutes, yielding highly purified free amino oligonucleotide.

EXAMPLE 11

Synthesis of 3'>HO—CpApTpGpCpTpGpT—NH₂<5' using 5'-N (9-fluorenylmethyloxycarbonyl)-5'-amino-5'-deoxythymidine-3,-O-methyl-N, N-diisopropylamino phosphoramidite and 5'-N-p-anisyldiphenylmethyl-5'-amino-5'-deoxythymidine-3'-O-methyl-N, N-diisopropylamino phosphoramidite ing", Setlow, A., and Hollander, J. K., eds., vol. 4, pp. 1–17, Plenum Press, New York (1982)). The 3'-O-methyl-N,N-diisopropylamino phosphoramidites of 5'-O-dimethoxytritylthymidine, 5'-O-dimethoxytrityl-N⁶-benzoyl-2'-deoxyadenosine, 5'-O-dimethoxytrityl-N⁴-benzoyl-2'-deoxycytidine, and 5'-O-dimethoxytrityl-N²-isobutyryl-2'-deoxyguanosine were synthesized according to published procedures (McBridge, L. J., and Caruthers, M. H., *Tetrahedron Lett.* 24, 245–248 (1983)). Spectroscopic analysis of the yield of dimethoxytrityl

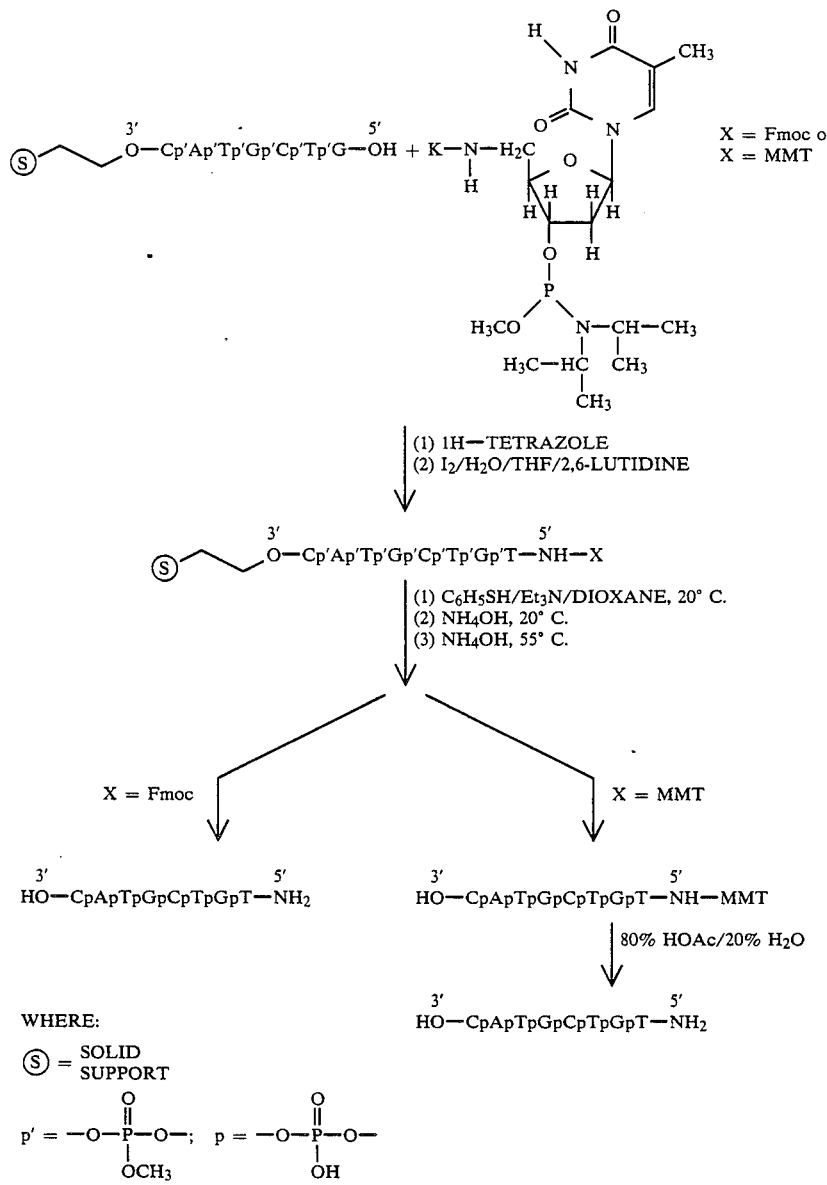

Reaction Scheme for Example 11

The oligodeoxyribonucleotide 3'>HO—CpApTpGpCpTpG—OH<5' was synthesized manually on an aminopropyl silica support (containing about 4 micromoles of bound 5'-O-dimethoxytrityl-N⁴-benzoyl-2'-deoxycytidine) using standard phosphoramidite DNA synthesis techniques (Caruthers, M. H., Beaucage, S. L., Becker, C., Efcavitch, W., Fisher, E. F., Gallupi, G., Goldman, R., deHaseth, F., Martin, F., Mateucci, M., and Stabinsky, Y., in "Genetic Engineercation after each cycle of the synthesis indicated an overall yield of 88.8% for the heptamer, for a stepwise yield of 97.7%. The support was then split into two equal portions. One portion was treated with the Fmoc-protected phosphoramidite, and the other the MMT-protected phosphoramidite. In each case, a twenty-fold excess of phosphoramidite and a one hundred-fold excess of 1H-tetrazole over support-bound oligodeoxyribonucleotide was used, with a six minute coupling reaction time and a three minute oxidation reaction time.

After washing and drying, each aliquot of the support was treated for one hour with triethylammonium thiophenoxide in dioxane, washed well, dried, and treated for four hours at room temperature with concentrated ammonium hydroxide in a tightly capped conical centrifuge tube. The supernatant was then decanted from the support, another aliquot of concentrated ammonium hydroxide added, and the solution heated at 55° C. for 16 hours in a tightly sealed tube (rubber septum). The DNA-containing solutions were then aliquoted into 1.5 ml Eppendorf tubes, lyophilized, and the resulting pellets dissolved in water. An aliquot of each oligonucleotide solution was then chromatographed on a RP HPLC system consisting of two Altex 110A pumps, a dual chamber gradient mixer, a Rheodyne injector, a Kratos 757 UV-VIS detector, and an Axxiom 710 controller. A Vydac C18 column (5 micron, 25 cm) was used.

Amino oligonucleotide derived from Fmoc-protected 5'-amino-5'-deoxythymidine phosphoramidite was chromatographed using a linear gradient of 10% buffer B/90% buffer A to 30% buffer B/70% buffer A over forty minutes, where buffer A is aqueous 0.1M triethylammonium acetate, pH 7/acetonitrile (98:2 v/v), and buffer B is aqueous 0.1M triethylammonium acetate, pH 7/ acetonitrile (50:50 v/v). The desired oligonucleotide eluted from the column at 17.5 minutes (1 ml/minute flow rate) under these conditions (260 nm UV detection).

Amino oligonucleotide derived from MMT-protected 5'-amino-5'-deoxythymidine phosphoramidite was first chromatographed as the dimethoxytritylated adduct, using a linear gradient of 20% buffer B/80% buffer A to 60% buffer B/40% buffer A over forty minutes (buffers A and B as described above). The product eluted at 39 minutes under these conditions 1 ml/minute flow rate). A preparative run of the MMT product was performed, the product collected and lyophilized, and the pellet treated with acetic acid/water (80:20 v/v) at room temperature for twenty minutes. Following lyophilization and re-dissolution in water, an aliquot was chromatographed using the same conditions as for the Fmoc-derived oligonucleotide. As expected, the product eluted at 17.5 minutes, the same retention time as was obtained for the Fmoc-derived oligonucleotide. Both purified amino oligonucleotides had UV spectra typical of DNA (major peak at 260 nm).

The following compounds may be employed in a similar fashion to prepare the corresponding 5'-amino oligonucleotides:

(1) 5'-N-(9-fluorenylmethyloxycarbonyl)-5'-amino-2',5'-dideoxyuridine-3'-O-beta-cyanoethyl-N,N-diisopropylamino phosphoramidite.

(2) 5'-N-(9-fluorenylmethyloxycarbonyl)-5'-amino-2',5'-dideoxyinosine-3'-O-methyl-N,N-diisopropylamino phosphoramidite.

(3) 5'-N-(9-fluorenylmethyloxycarbonyl)-5'-amino-N$^6$-benzoyol-2',5'-dideoxyadenosine-3'-O-methyl-N,N-diisopropylamino phosphoramidite.

(4) 5'-N-(9-fluorenylmethyloxycarbonyl)-5'-amino-N$^4$-benzoyl-2',5'-dideoxycytosine-3'-O-methyl-N,N-diisopropylamino phosphoramidite.

(5) 5'-N-(9-fluorenylmethyloxycarbonyl)-5'-amino-N$^2$-isobutyryl-2',5'-dideoxyguanosine-3'-O-methyl-N,N-dimethylamino phosphoramidite.

(6) 5'-N-(9-fluorenylmethyloxycarbonyl)-5'-amino-2'-tetrahydropyranyl-5'-deoxyuridine-3'-O-methyl-N,N-diisopropylamino phosphoramidite.

(7) 5'-N-(9-fluorenylmethyloxycarbonyl)-5'-amino-2'-tetrahydropyranyl-5'-deoxyinosine-3'-O-methyl morpholino phosphoramidite.

(8) 5'-N-(9-fluorenylmethyloxycarbonyl)-5'-amino-2'-tetrahydropyranyl-N$^6$-benzoyl-5'-deoxyadenosine-3'-O-methyl-N,N-diisopropylamino phosphoramidite.

(9) 5'-N-(9-fluorenylmethyloxycarbonyl)-5'-amino-2'-tetrahydropyranyl-N$^4$-benzoyl-5'-deoxycytosine-3'-O-beta-cyanoethyl morpholino phosphoramidite.

(10) 5'-N-(9-fluorenylmethyloxycarbonyl)-5'-amino-2'-tetrahydropyranyl-N$^2$-isobutyryl-5'-deoxyguanosine-3'-O-methyl-N,N-diisopropylamino phosphoramidite

(11) 5'-N-(9-fluorenylmethyloxycarbonyl)-5'-amino-5'-deoxythymidine-3'-O-p-nitrophenethyl-N,N-dimethylamino phosphoramidite.

(12) 5'-N-(9-fluorenylmethyloxycarbonyl)-5'-amino-2',5'-dideoxyuridine-3'-O-methyl-N,N-diisopropylamino phosphoramidite.

(13) 5'-N-(9-fluorenylmethyloxycarbonyl)-5'-amino-2',5'-dideoxyinosine-3'-O-betacyanoethyl-N,N-dimethylamino phosphoramidite.

(14) 5'-N-p-anisyldiphenylmethyl-5'-amino-5'-deoxythymidine-3'-O-methyl-N,N-diisopropylamino phosphoramidite.

(15) 5'-N-p-anisyldiphenylmethyl-5'-amino-5'-deoxythymidine-3'-O-methyl-N,N-dimethylamino phosphoramidite.

(16) 5'-N-p-anisyldiphenylmethyl-5'-amino-5'-deoxythymidine-3'-O-methyl morpholino phosphoramidite.

(17) 5'-N-p-anisyldiphenylmethyl-5'-amino-5'-deoxythymidine-3'-O-beta-cyanoethyl morpholino phosphoramidite.

(18) 5'-N-p-anisyldiphenylmethyl-5'-amino-5'-deoxythymidine-3'-O-p-nitrophenethyl-N,N-dimethylamino phosphoramidite.

(19) 5'-N-p-anisyldiphenylmethyl-5'-amino-5'-deoxythymidine-3'-O-betacyanoethyl-N,N-dimethylamino phosphoramidite.

(2) Synthesis in aqueous solution of oligodeoxyribonucleotides containing a fluorescent moiety on the 5'-terminus.

The presence of a nucleophilic aliphatic amino group on the 5'-end of an oligonucleotide allows for further reaction of the amino DNA with a variety of electrophilic reagents, notably amino reactive fluorescent dye derivatives. Such dye derivatives include, but are not restricted to, fluorescein isothyiocyanate, tetramethylrhodamine isothiocyanate, eosin isothiocyanate, erythrosin isothiocyanate, rhodamine X isothiocyanate, lissamine rhodamine B sulfonyl chloride, Texas Red, Lucifer Yellow, acridine-9-isothiocyanate, pyrene sulfonyl chloride, 7-diethylamino-4-methylcoumarin isothiocyanate, and 4-fluoro-and 4-chloro-7-nitrobenz-2-oxa-1,3-diazole and their derivatives, such as succinimidyl 12-(N-methyl-N-(7-nitrobenz-2-oxa-1,3-diazol-4-yl)) aminododecanoate. The resultant dye-oligonucleotide conjugates may then be used for a variety of diagnostic or detection purposes.

The basic procedure used for attaching dye molecules to an amino oligonucleotide is to combine the amino DNA and the dye in an aqueous (or aqueous/organic) solution buffered at pH 9, allow it to stand at room temperature for several hours, and then to purify the product in two stages. Excess unreacted dye is removed from dye-DNA conjugate and unreacted DNA by gel filtration. After lyophilization, pure dye-DNA conjugate is obtained using RP HPLC.

EXAMPLE 12

Conjugation of fluorescein-5-isothiocyanate with
3′>HO—CpApTpGpCpTpGpTTT—NH$_2$<5′ species at 29 minutes and the desired fluorescent product (the major product) at 33 minutes (UV detection at 260 nm, fluorescent excitation at 240 nm and detection using a 525 nm band pass filter). The purified fluorescent oligonucleotide had a UV absorbance maximum at 260 nm (characteristic of DNA) and a visible absorbance maximum at 496 nm (characteristic of fluorescein).

Similar conjugates can be obtained by using Texas

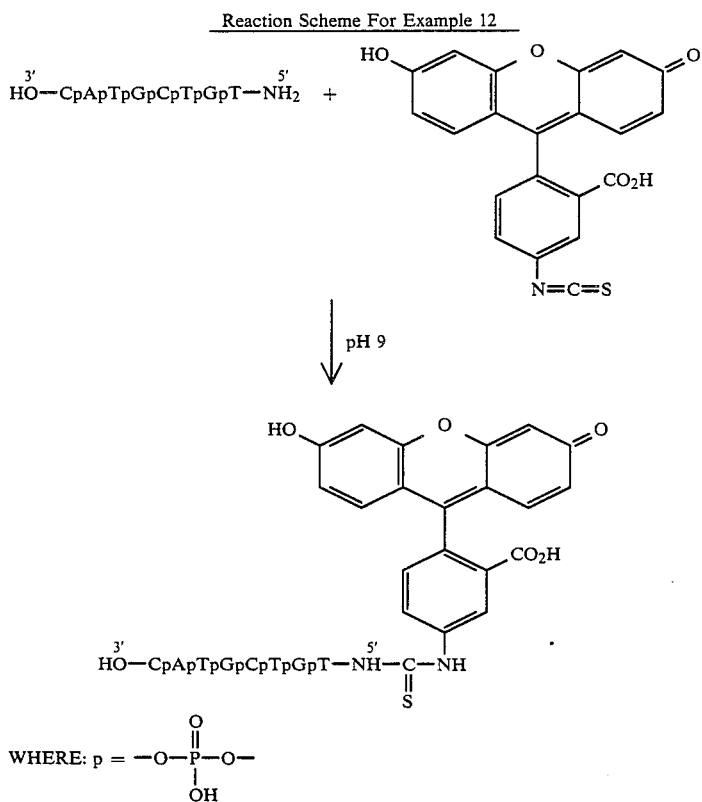

Reaction Scheme For Example 12

5′-amino oligonucleotide was synthesized as described in Example 11. The purified amino oligonucleotide (75 ul of a 1200 ug/ml solution in water) is diluted with water (105 ul) and 1M aqueous sodium bicarbonate/sodium carbonate buffer, pH 9 (50 ul). A solution of fluorescein-5-isothiocyanate (FITC) in DMF (20 mg/ml, 20 ul) is added, and the yellow solution mixed well and allowed to sit in the dark overnight at room temperature (about 12–16 hours). The reaction mixture was then applied to a column (10 ml) of Sephadex G-25 (Pharmacia Fine Chemicals) packed in water in a 10 ml disposable plastic pipet, and the column was eluted with water. The fast moving yellow band (fluorescent under long wave UV) that eluted with the void volume of the column was collected. Unreacted dye remained nearly immobile at the top of the column. The crude dye-DNA conjugate was then lyophilized, dissolved in water, and subjected to RP HPLC. A Kratos FS970 LC fluorometer was used in conjunction with the UV detector in the system described in Example 11 to identify the desired product. A linear gradient of 10% buffer B/90% buffer A to 30% buffer B/70% buffer A over thirty minutes was used (buffers A and B are as described in Example 11). A small amount (<10%) of the starting amino oligonucleotide was eluted at 17.5 minutes (1 ml/minute flow rate), followed by a small amount of a fluorescent Red, tetramethyl rhodamine isothiocyanate, eosin isothiocyanate, erythrosin isothiocyanate, rhodamine X isothiocyanate, lissamine rhodamine B sulfonyl chloride, pyrene sulfonyl chloride, 7-diethylamino-4-methylcoumarin isothiocyanate, Lucifer Yellow, acridine-9-isothiocyanate, 4-fluoro-7-nitrobenz-2-oxa-1,3-diazole, and 4-chloro-7-nitrobenz-2-oxa-1,3-diazole.

(3) Synthesis of oligodeoxyribonucleotides containing a fluorescent moiety on the 5′-terminus utilizing a solid support.

The two step purification described in Example 12 can be avoided by reacting the fluorescent dye directly with the oligonucleotide containing a free 5′-amino group while it is still covalently linked to the support. In this case, experience has determined that the oligonucleotide must be assembled using the beta-cyanoethyl phosphorous-protected phosphoramidite monomers. This is necessary as the beta-cyanoethyl groups may be removed from the oligonucleotide phosphate triesters to give phosphate diesters under basic, anhydrous conditions, such as 20% (v/v) tertiary amine in anhydrous pyridine or 0.5M 1,8-diazabicyclo [5.4.0]undec-7-ene (DBU) in anhydrous pyridine, at room temperature. Such treatment does not otherwise affect the DNA, nor does it cleave appreciable amounts from the support if strictly anhydrous conditions are observed. Generation of diesters is critical as the triester-containing oligonucleotide having a free amino group is unstable to the basic conditions needed to effect rapid reaction with the dye, and degrades to an as yet uncharacterized DNA-like species no longer having an accessible amino terminus. Conversion to the diester form retards this degradation.

It is also necessary to employ an acid-labile protecting group such as p-anisyldiphenylmethyl (MMT) on the 5'-amino-5'-deoxythymidine phosphoramidite to introduce the 5'-amino terminus into the oligonucleotide. This is required as the MMT group is stable to the basic conditions needed to remove the phosphate protecting groups, where it is needed to prevent the basic degradation of the DNA described previously, but can subsequently be removed using mildly acidic conditions under which the DNA remains linked to the support, thus affording a free amino oligonucleotide for reaction with dye.

Dye conjugation to the amino oligonucleotide is carried out using an excess of dye (ten-to-one hundred-fold) in concentrated solution in anhydrous N,N-dimethylformamide/tertiary amine, preferably N,N-diisopropylethylamine (90:10 v/v) or triethylamine (80:20 v/v). After twelve to twenty-four hours, the excess dye is washed away, the dye-DNA conjugate is cleaved from the support, and the base-protecting groups are removed using concentrated ammonium hydroxide under the standard conditions described in Example 11. The product is then purified by RP HPLC.

EXAMPLE 12

Conjugation of eosin-5-isothiocyanate and Texas Red with 3'>HO—TpTpTpTpTpTpT—NH$_2$<5' on a solid support

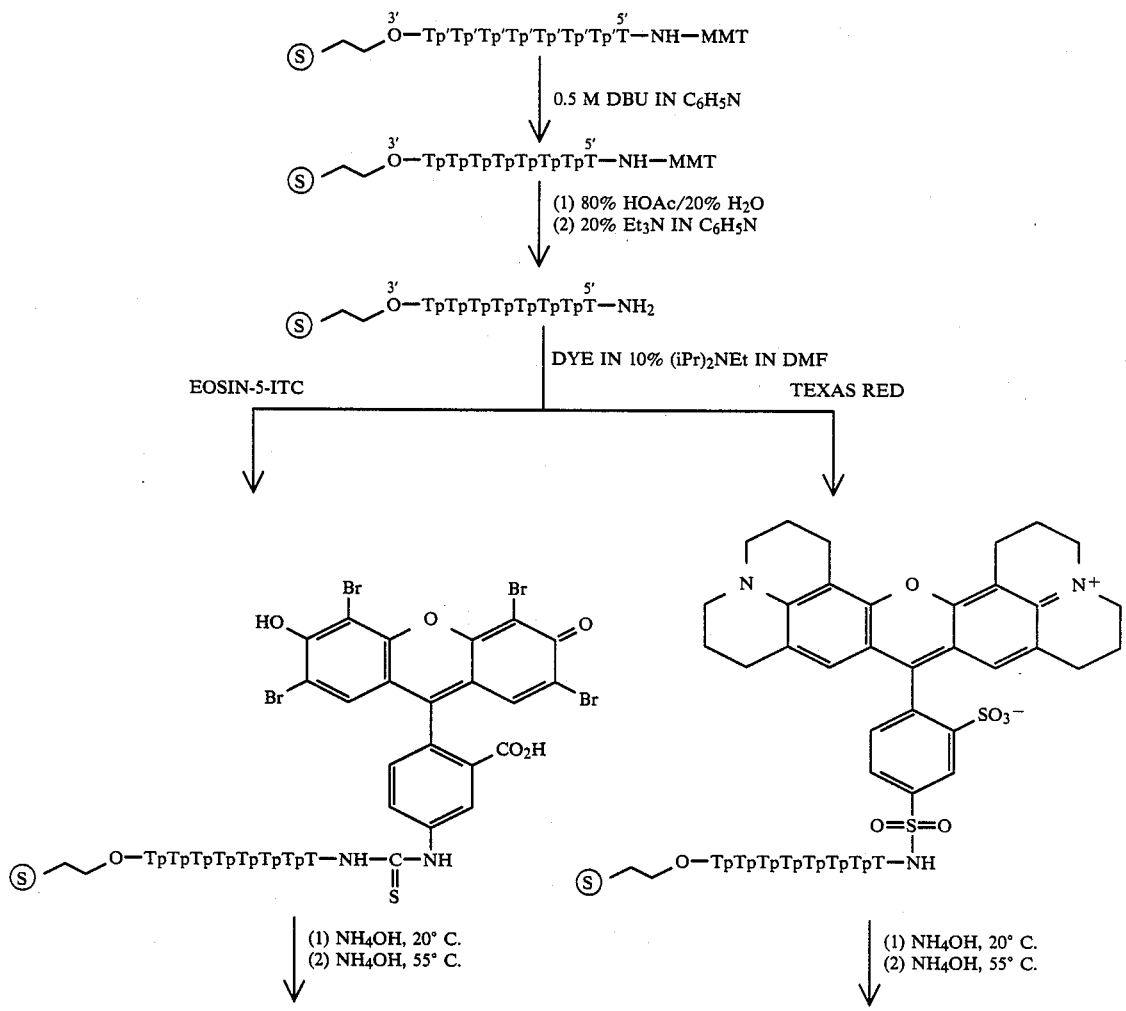

-continued
Reaction Scheme for Example 13

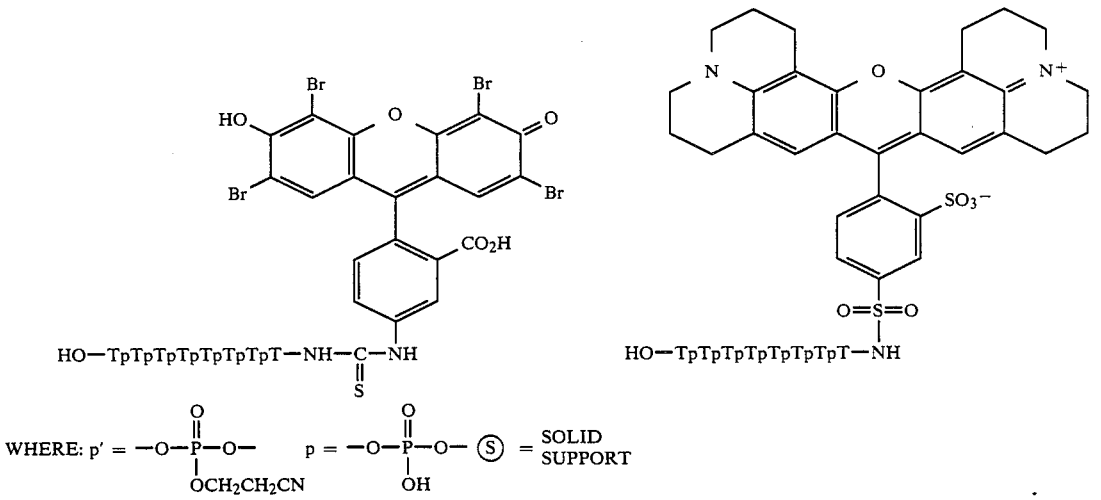

HO—TpTpTpTpTpTpTpT—NH—C(=S)—NH—  HO—TpTpTpTpTpTpT—NH—

WHERE: p' = —O—P(=O)(OCH₂CH₂CN)—O—    p = —O—P(=O)(OH)—O—   Ⓢ = SOLID SUPPORT

The oligodeoxyribonucleotide 3'>HO-TpTpTpTpTpTo-OH<5' was synthesized as described in Example 11 on a controlled pore glass support on a one micromole scale using beta-cyanoethyl-protected phosphoramidites (obtained from American BioNuclear Corporation or synthesized as described in Example 6). Analysis of the yield of dimethoxytrityl cation after each cycle indicated an overall yield of 89.6% for the hexamer, for a stepwise yield of 97.8%. The final addition of 5'-N-p-anisyldiphenylmethyl-5'-amino5'-deoxy-thymidine-3'-O-beta-cyanoethyl-N,N-diisopropylamino phosphoramidite was performed as described in Example 11.

An aliquot of the fully protected, support-bound amino oligonucleotide containing about 0.5 umole of DNA (about 20 mg of support) was then treated with a mixture of a 5% (w/v) solution of N,N-dimethylaminopyridine (Aldrich Chemical Company) in anhydrous pyridine (500 ul) and a 10% (w/v) solution of p-anisyldiphenylmethyl chloride in anhydrous pyridine (500 ul) for one hour at room temperature. This was done in order to insure that all terminal amino groups were protected, and is probably unnecessary if the dye conjugation is to be performed soon after the oligonucleotide synthesis. The support was next washed well with dry pyridine and treated for two hours with 0.5M DBU in anhydrous pyridine at room temperature. The support was again washed well with pyridine and then with diethyl ether and air dried. An aliquot (about 4 mg) was taken and cleaved, deprotected, and subjected to RP HPLC as usual as a control.

The dry support-bound MMT-protected amino oligonucleotide was detritylated for twenty minutes at room temperature with acetic acid/water (80:20 v/v). The support was then washed with water and methanol, and treated for two minutes with triethylamine in anhydrous pyridine (20:80 v/v) to generate the free amine from the acetate salt. It was washed with pyridine and ether and air and vacuum dried. An aliquot (4 mg) was taken and cleaved, deprotected, and subjected to RP HPLC as usual as a control.

The dye conjugation reactions were carried out in 1.5 ml Eppendorf tubes. Dyes were obtained from Molecular Probes Inc., Junction City, Oreg. About 0.1 umole of support-bound amino oligonucleotide (4–5 mg) was treated with either eosin-5-isothiocyanate (3.5 mg, a 50-fold excess) or Texas Red (2.4 mg, a 38-fold excess) in anhydrous DMF containing 10% (v/v) N,N-diisopropylethylamine (50 ul). The reactions were allowed to proceed in the dark for 12 to 16 hours at room temperature. The reaction mixture was then transferred to a small glass-fritted funnel and washed well with DMF, methanol, and ether, and air dried. At this point, the eosin-conjugated support was pink and the Texas Red-conjugated support was purple. Both supports fluoresced strongly under long wave UV light.

Each dye-DNA conjugate was cleaved from its support as described in Example 11 (four hours at room temperature in concentrated ammonium hydroxide), and subjected to base-deprotection conditions (twelve hours at 55° C. in concentrated ammonium hydroxide). Although unnecessary for a poly-T oligonucleotide, this latter treatment was performed to test the effect of the treatment on the dye moiety and the dye-DNA linkage. The strongly fluorescent orange (eosin) and pink-red (Texas Red) dye-DNA solutions were then lyophilized, dissolved in water, and each fluorescent oligonucleotide purified by RP HPLC using a linear gradient of 10% buffer B/90% buffer A to 30% buffer B/70% buffer A over ten minutes, then 30% buffer B/70% buffer A to 60% buffer B/40% buffer A over ten minutes (buffers A and B as described in Example 11).

HPLC analysis of the two dye-oligonucleotide conjugates indicated that, in the case of eosin-5-isothiocyanate, the reaction had proceeded to about 80% completion, as judged from the disappearance of starting amino oligonucleotide, while in the case of Texas Red, a sulfonyl chloride, the reaction had proceeded to only about 20–30% completion. In each chromatogram, a peak representing underivatized amino oligonucleotide was observed at 16 minutes. The desired eosin-DNA conjugate eluted from the column at 25 minutes, and the Texas Red-DNA conjugate at 29.5 minutes. Control HPLC analyses of the starting amino oligonucleotide and of each fluorescent oligonucleotide separately synthesized using the solution method described in Example 8 confirmed the above assignments. In addition, while the Texas Red-oligonucleotide appeared unharmed by the deprotection conditions, the eosin-oligonucleotide did appear to have suffered a small amount of degradation. However, in both cases, the overall yield of dye-DNA conjugate using the solid phase-method was as good or better than that using the solution method, and the workup and purification was much simpler. The UV-visible spectrum of each purified dye-DNA conjugate showed two major peaks, as anticipated: for the eosin-oligonucleotide, one at 262 nm (DNA absorbance), and one at 524 nm (dye absorbance); and for the Texas Red-oligonucleotide, one at 262 nm (DNA absorbance), and one at 596 nm (dye absorbance).

Similar conjugates can be obtained by using fluorescein isothiocyanate, tetramethyl rhodamine isothiocyanate, eosin isothiocyanate, erythrosin isothiocyanate, rhodamine X isothiocyanate, lissamine rhodamine B sulfonyl chloride, pyrene sulfonyl chloride, 7-diethylamino-4-methylcoumarin isothiocyanate, 4-fluoro-7-nitrobenz-2-oxa-1,3-diazole, 4-chloro-7-nitrobenz-2-oxa-1,3-diazole, acridine-9-isothiocyanate, and Lucifer Yellow.

(4) Synthesis of oligodeoxyribonucleotides containing one or more internal aliphatic amino groups.

The trifluoracetyl-protected (Tfa-protected) 2'-amino-2'-deoxyuridine-3'-O-phosphoramidites described in the section entitled "Composition of Matter No. 4" can be used to synthesize oligodeoxyribonucleotides containing one or more free amino groups at internal positions in the DNA oligomer. This is possible since the position of the amino group (that is, on the 2'-carbon atom of the sugar ring) in these compounds is not involved in the formation of the 3',5'-phosphodiester backbone of the DNA chain. As such, these compounds may be coupled to the 5'-hydroxyl of a growing oligodeoxyribonucleotide attached to a solid support using the standard phosphoramidite DNA synthesis techniques described in Example 11. Unlike the protected 5'-amino-5'-deoxythymidine compounds, whose use forces the termination of the growing DNA chain due to the presence of the amino group on the 5'-terminus, the 5'-O-di-p-anisylphenylmethyl group present on the 5'-hydroxyl of the Tfa-protected 2'-amino-2'deoxyuridine compounds may be removed in the next cycle of the synthesis allowing for further elongation of the synthetic oligonucleotide by the usual procedure. Since a Tfa-protected 2'-amino2'-deoxyuridine unit can be inserted at any position in the chain, the resultant oligomer can contain any desired number of reactive amino groups.

These compounds can be coupled to a growing DNA chain using the chemistry outlined in Example 11; however, the presence of a group other than hydrogen at the 2'-position necessitates the use of longer coupling times to achieve a coupling efficiency similar to that observed using normal deoxyribonucleotide phosphoramidites. Once again, a ten-to-twenty-fold excess of phosphoramidite and a fifty-to-one hundred-fold excess of 1H-tetrazole over support-bound oligonucleotide are required; the larger excesses are strongly preferable in this case. Coupling times using these quantities are generally one to one and one-half hours, as opposed to the six minutes used for normal phosphoramidite couplings. Since the Tfa-protected 2'-amino-2'-deoxyuridine phosphoramidites appear to undergo some degradation during this longer coupling time, two or three shorter couplings (twenty to thirty minutes each) are preferable to one extended coupling. Under these conditions, the Tfa-protected 2'-amino-2'-deoxyuridine-3'-O-phosphoramidites (Examples 9 and 10) routinely couple in better than 80% yield, and generally in better than 85% yield.

The oligonucleotide product containing one or more internal amino groups is then obtained using the standard cleavage and deprotection conditions outlined in Example 11. Since the Tfa group is base-labile, it is easily removed during the concentrated ammonium hydroxide treatments, yielding an oligonucleotide product containing the desired number of free amino groups. After lyophilization, the product DNA may be purified either by RP HPLC or by gel electrophoresis, as described previously. Furthermore, the crude product DNA can be obtained containing a 5'-O-di-p-anisylphenylmethyl group, thus simplifying RP HPLC purification in a manner analogous to that described for the 5'-N-p-anisyldiphenylmethyl group.

EXAMPLE 14

Synthesis of
3'>HO—CpApTpGpCpU(2'—NH$_2$)pGpT—OH<5'
using
5'-O-di-p-anisylphenylmethyl-2'-N-trifluoroacetyl-2'-amino-2'-deoxyuridine-3'-O-methyl-N,N-diisopropylamino phosphoramidite, and of
3'>HO—CpApTpGpCpU(2'—NHCOCH$_2$NH$_2$)pGpT—OH<5' using
5,-O-di-p-anisylphenylmethyl-2'-N-(N-trifluoroacetylglycyl)-2'-amino-2'-deoxyuridine-3'-O-methyl-N,N-diisopropylamino phosphoramidite

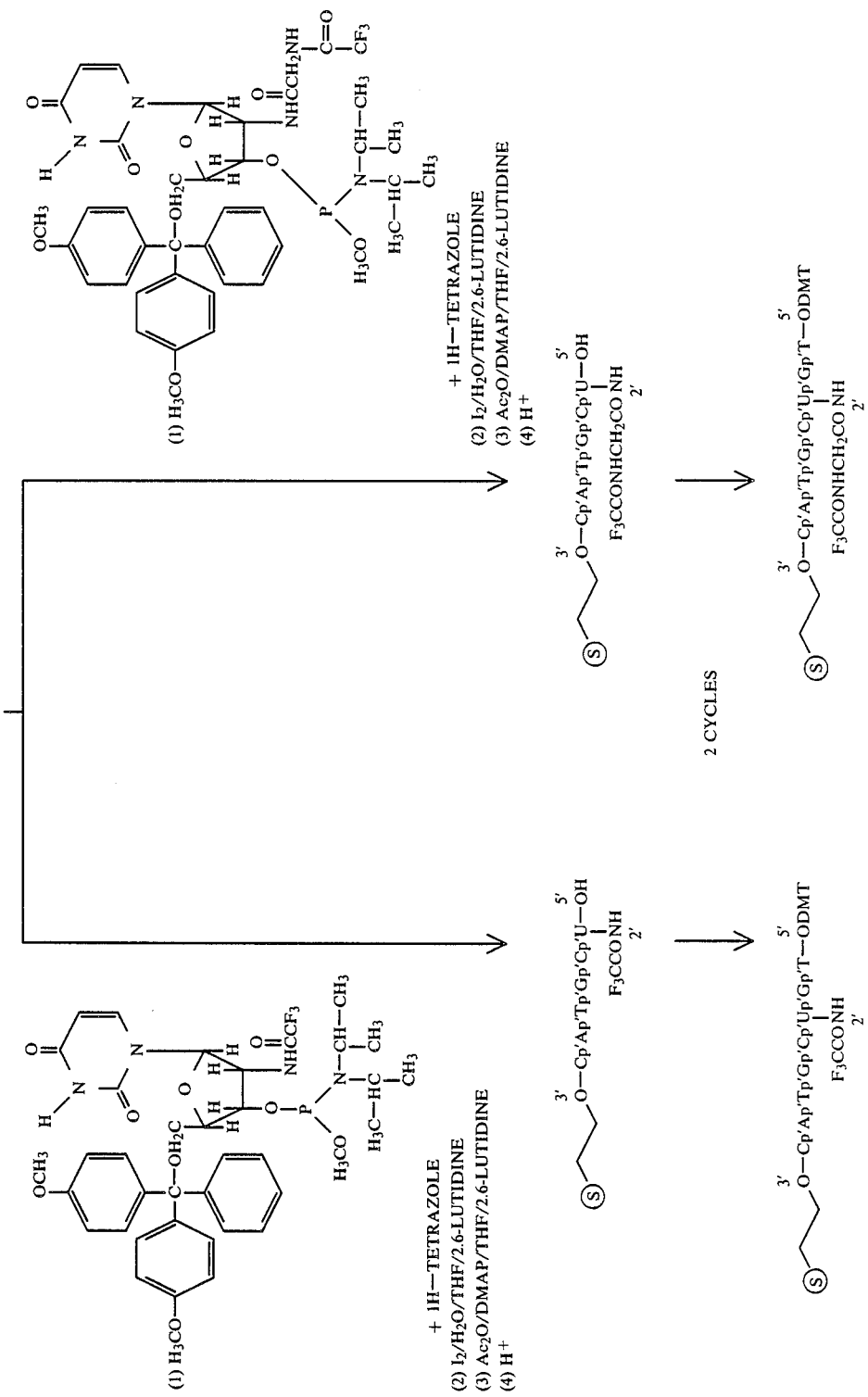

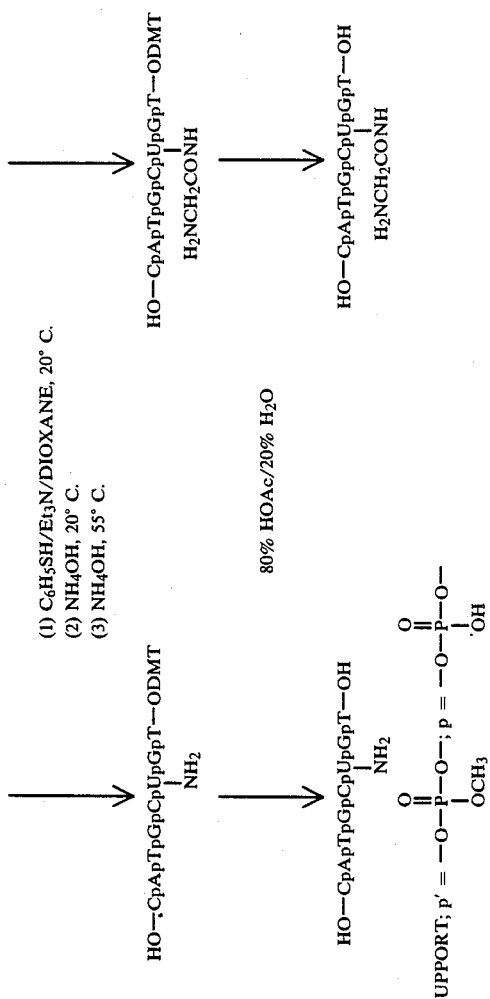

The oligodeoxyribonucleotide 3'>HO—CpApTpG-pC—OH<5' was synthesized manually on an aminopropyl silica support as described in Example 11. The support was then split into two equal portions. One portion was used in a coupling with 5'-O-di-p-anisylphenylmethyl-2'-N-trifluoroacetyl-2'-amino-2'-deoxyuridine (DMT-TfaNHdU) phosphoramidite, and the other in a coupling with 5'-O-di-p-anisylphenylmethyl-2'-N-(N-trifluoroacetylglycyl)-2'-amino-2'-deoxyuridine (DMT-TfaGlyNHdU) phosphoramidite. In each case, two sequential couplings of thirty minutes each were performed prior to the oxidation reaction, with the support being washed well with anhydrous acetonitrile between couplings. In each coupling, a twenty-fold excess of phosphoramite and a one-hundred-fold excess of 1H-tetrazole were used. Under these conditions, both the DMT-TfaNHdU phosphoramidite and the DMT-TfaGlyNHdU phosphoramidite coupled in 83-85% yield (as judged by the yield of dimethyoxytrityl cation after this cycle). After a three minute oxidation reaction and a three minute capping reaction, the last two nucleotide phosphoramidites were coupled to the amino uridine-containing oligonucleotide. In each case, the first of these two couplings proceeded in better than 98% yield; the final di-p-anisylphenylmethyl group was retained on the 5'-end of each oligonucleotide in order to simplify RP HPLC purification.

After washing and drying, each aliquot of the support-bound oligonucleotide was treated under the standard cleavage and deprotection conditions described in Example 11, lyophilized, and dissolved in water. An aliquot of each solution was then subjected to RP HPLC analysis using the system described in Example 11. A linear gradient of 20% buffer B/80% buffer A to 60% buffer B/40% buffer A (buffers A and B as described in Example 11) over forty minutes was used to purify each tritylated adduct. Both the U(2'—NH$_2$)-containing oligonucleotide and the U(2'—NHCOCH$_2$NH$_2$)-containing oligonucleotide eluted at 39 minutes under these conditions (1 ml/minute flow rate). A preparative purification was performed for each oligonucleotide, the product collected and lyophilized, and the pellet treated with acetic acid/water (80:20 v/v) for thirty minutes at room temperature to remove the 5'-di-p-anisylphenylmethyl group. Following lyophilization and re-dissolution in water, an aliquot of each solution was chromatographed using a linear gradient of 10% buffer B/90% buffer A to 30% buffer B/70% buffer A over thirty minutes. Under these conditions (1 ml/ minute flow rate), the U(2'—NH$_2$)-containing octamer eluted cleanly at 18 minutes (UV detection at 260 nm), while the U(2'—NHCOCH$_2$NH$_2$)-containing octamer eluted slightly less cleanly at 19 minutes. No peak eluting at 18 minutes was seen in this latter chromatogram, indicating that little if any of the glycine moiety had been hydrolyzed from the DNA by any chemical treatment during the synthesis. Both purified 2'-amino oligonucleotides had UV spectra typical of DNA (major peak at 260 nm).

The following compounds may be employed in a similar fashion to prepare the corresponding 2' amino oligonucleotides:

(1) 5'-O-di-p-anisylphenylmethyl-2'-N-trifluoroacetyl-2'-amino-2'-deoxyuridine-3'-O-beta-cyanoethyl-N,N-diisopropylamino phosphoramidite.

(2) 5'-O-di-p-anisylphenylmethyl-2'-N-trifluoroacetyl-2'-amino-2'-deoxyinosine-3'-O-methyl-N,N-diisopropylamino phosphoramidite.

(3) 5'-O-di-p-anisylphenylmethyl-2'-N-trifluoroacetyl-2'-amino-2'-N$^6$-benzoyl-2'-deoxyadenosine-3'-O-methyl-N,N-diisopropylamino phosphoramidite.

(4) 5'-O-di-p-anisylphenylmethyl-2'-N-trifluoroacetyl-2'-amino-2'-N$^4$-benzoyl-2'-deoxycytosine-3'-O-methyl-N,N-diisopropylamino phosphoramidite.

(5) 5'-O-di-p-anisylphenylmethyl-2'-N-trifluoroacetyl-2'-amino-2'-N$^2$-isobutyryl-2'-deoxyguanosine-3'-O-methyl-N,N-diisopropylamino phosphoramidite.

(6) 5'-O-di-p-anisylphenylmethyl-2'-N-(9-fluorenylmethyl oxycarbonyl)-2'-amino-2'-deoxyuridine-3'-O-methyl-N,N-diisopropylamino phosphoramidite.

(7) 5'-O-di-p-anisylphenylmethyl-2'-N-(N-trifluoroacetylglycyl)-2'-amino-2'-deoxyuridine-3'-O-beta-cyanoethyl-N,N-diisopropylamino phosphoramidite.

(8) 5'-O-di-p-anisylphenylmethyl-2'-N-(N-trifluoroacetylglycyl)-2'-amino-2'-deoxyuridine-3'-O-methyl-N,N-dimethylamino phosphoramidite.

(9) 5'-O-di-p-anisylphenylmethyl-2'-N-(N-trifluoroacetylglycyl)-2'-amino-2'-deoxyuridine-3'-O-methyl-morpholino phosphoramidite.

(10) 5'-O-di-p-anisylphenylmethyl-2'-N-(N-trifluoroacetylglycyl)-2'-amino-2'-deoxyuridine-3'-O-beta-cyanoethylmorpholino phosphoramidite.

(11) 5'-O-di-p-anisylphenylmethyl-2'-N-(N-trifluoroacetylglycyl)-2'-amino-2'-deoxyuridine-3'-O-p-nitrophenethyl-N,N-dimethylamino phosphoramidite.

(12) 5'-O-di-p-anisylphenylmethyl-2'-N-(N-trifluoroacetyl-glycyl)-2'-amino-2'-deoxyuridine-3'-O-beta-cyanoethyl-N,N-dimethylamino phosphoramidite.

(13) 5'-O-di-p-anisylphenylmethyl-2'-N-(N-trifluoroacetylglycyl)-2'-amino-2'-deoxyinosine-3'-O-methyl-N,N-diisopropylamino phosphoramidite.

(14) 5'-O-di-p-anisylphenylmethyl-2'-N-(N-trifluoroacetylglycyl)-2'-amino-N$^6$-benzoyl-2'-deoxyadenosine-3'-O-methyl-N,N-diisopropylamino phosphoramidite.

(15) 5'-O-di-p-anisylphenylmethyl-2'-N-(N-trifluoroacetylglycyl)-2'-amino-N$^4$-benzoyl-2'-deoxycytosine-3'-O-methyl-N,N-diisopropylamino phosphoramidite.

(16) 5'-O-di-p-anisylphenylmethyl-2'-N-(N-trifluoroacetyl-glycyl)-2'-amino-N$^2$-isobutyryl-2'-deoxyguanosine-3'-O-methyl-N,N-diisopropylamino phosphoramidite.

(17) 5'-O-di-p-anisylphenylmethyl-2'-N-(N-9-fluorenylmethyloxycarbonyl-glycyl)-2'-amino-2'-deoxyuridine-3'-O-methyl-N,N-diisopropylamino phosphoramidite.

(5) Synthesis in aqueous solution of oligodeoxyribonucleotides containing one or more fluorescent moieties at internal 2'-positions.

As has been described in Section 2, the presence of an aliphatic amino group in an oligonucleotide allows for further reaction of the DNA with a variety of reagents. In the case of fluorescent dyes, enhanced detection sensitivity may be achieved by conjugating more than one dye molecule to an oligonucleotide, thus increasing the amount of fluorescence per oligomer. The ability to incorporate any desired number of amino groups into an oligonucleotide via the 2'-amino-2'-deoxyuridine phosphoramidites can be utilized to achieve this enhancement.

The basic procedure for conjugating a fluorescent dye to a 2'-amino oligonucleotide is the same as that described in Example 12.
EXAMPLE 15
Conjugation of fluorescein-5-isothiocyanate with
3'>HO—CpApTpGpCpU(2'—NH$_2$)pGpT—OH<5'
and
3'>HO—CpApTpGpCpU(2'—NHCOCH$_2$NH$_2$)pGpT—Oh<5'
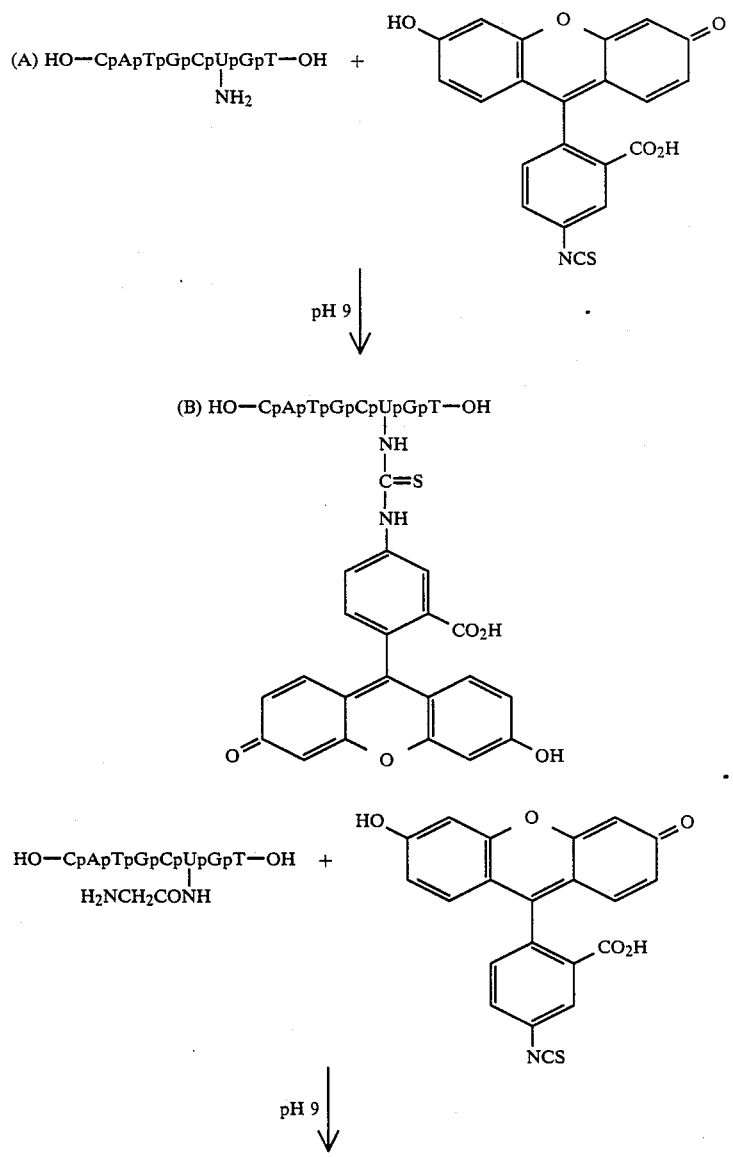

Reaction Scheme for Example 15

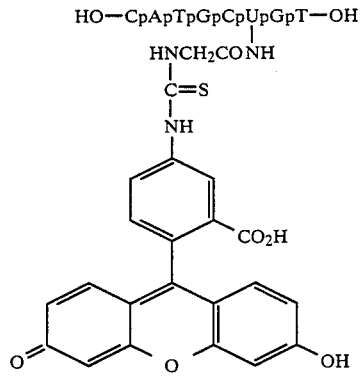

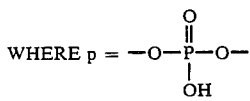

The 2'-amino oligonucleotides were synthesized as described in Example 14. Each of the purified amino oligonucleotides (75 ul of a 600–1000 ug/ml solution in water) was diluted with water (105 ul) and 1M aqueous sodium bicarbonate/sodium carbonate buffer, pH 9 (50 ul) in 1.5 ml Eppendorf tubes. A solution of fluorescein-5-isothiocyanate (FITC) in DMF (20 mg/ml, 20 ul) was added, and the yellow solution mixed well and allowed to stand at room temperature overnight in the dark (about 12–16 hours). Each reaction mixture was then applied to a separate column (10 ml) of Sephadex G-25 packed in water in a 10 ml disposable plastic pipet, and the column was eluted with water. The fast moving yellow band (fluorescent under long wave UV) that eluted with the void volume of the column was collected in each case. The crude dye-DNA conjugates were then lyophilized, dissolved in water, and subjected to RP HPLC using the system described in Example 12. A linear gradient of 10% buffer B/90% buffer A to 30% buffer B/70% buffer A over thirty minutes was used (buffers A and B as described in Example 11), and a flow rate of 1 ml/minute.

In the case of the U(2'—NH—FITC)-containing oligonucleotide, two major peaks were observed. The starting 2'-amino oligonucleotide eluted at 18 minutes as expected, while the fluorescent product dye-oligonucleotide conjugate eluted at 26 minutes (UV detection at 260 nm, fluorescent excitation at 240 nm and detection using a 525 nm band-pass filter). The fluorescent product accounted for about 50% of the total amount of amino-containing DNA present in the sample.

In the case of the U(2'—NHCOCH$_2$NH—FITC)-containing oligonucleotide, three major peaks were observed. The starting 2'-amino oligonucleotide eluted at 20 minutes as expected. The second major peak at 20.5 minutes was also observed as a contaminant in the chromatogram of the starting 2'-amino oligonucleotide. The fluorescent product dye-oligonucleotide conjugate eluted at 28 minutes. In this case, however, the fluorescent product accounted for at least 90% of the total amount of amino-containing DNA in the sample. The substantially higher degree of conjugation can be attributed to the presence of the glycine moiety on the 2'-amino group. Not surprisingly, moving the reactive amino group away from the sugar ring and thus reducing the steric hindrance to its access by dye increases the amount of ye-DNA conjugate obtained. Therefore, it is possible to control the degree of reactivity of the amino group by adjusting the length of the spacer, thus controlling its distance from the sugar ring.

Both purified fluorescent oligonucleotides had a UV absorbance maximum at 260 nm (characteristic of DNA) and a visible absorbance maximum at 496 nm (characteristic of fluorescein).

The above can also be carried out by using Texas Red, tetramethyl rhodamine isothiocyanate, eosin isothiocyanate, erythrosin isothiocyanate, rhodamine X isothiocyanate, lissamine rhodamine B sulfonyl chloride, Lucifer Yellow, acridine-9-isothiocyanate, pyrene sulfonyl chloride, 7-diethylamino-4-methylcoumarin isothiocyanate, 4-fluoro-7-nitrobenz-2-oxa-1,3-diazole, and 4-chloro-7-nitrobenz-2-oxa-1,3-diazole.

Having fully described the invention, it is intended that it be limited solely by the lawful scope of appended claims.

We claim:

1. Protected amino nucleosides having the formula:

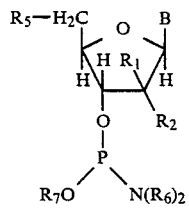

wherein B is selected from the group consisting of adenine, guanine, thymine, cytosine, uracil, and inosine, $R_1$, $R_2$ and $R_5$ are either H, OR, or NHR', with the proviso that one of $R_1$, $R_2$ and $R_5$ is NHR', and only $R_5$ can be OH, wherein R is a monovalent protecting organic group containing from 1 to about 25 carbon atoms, R' is a nitrogen protecting group; $R_6$ is lower alkyl or heterocyclic, and $R_7$ is lower alkyl, cyano lower alkyl, halo lower alkyl, or nitrophenyl-lower alkyl.

2. Protected 5'-amino nucleoside phosphoramidites having the formula:

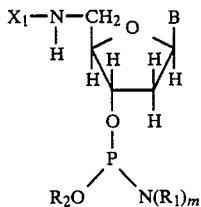

wherein B is selected from the group consisting of thymine and uracil; $X_1$ is selected from trifluoroacetyl, 9-fluorenylmethyloxycarbonyl, p-anisyldiphenylmethyl, triphenylmethyl, and protected amino acyl having the formula:

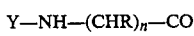

wherein Y is selected from the group consisting of trifluoroacetyl, 9-fluorenylmethyloxycarbonyl, p-anisyldiphenylmethyl, and triphenylmethyl;

R is an amino acid side chain or hydrogen when n=1; and R is hydrogen when n is an integer from 2 to 100;

$R_1$ is selected from the group consisting of lower alkyl (in which case m=2) and heterocyclic (in which case m=1), and $R_2$ is selected from the group consisting of methyl, beta-cyanoethyl, p-nitrophenethyl, o-chlorophenyl, or p-chlorophenyl.

3. The compounds of claim 2 wherein $X_1$ is trifluoroacetyl.

4. The compounds of claim 2 wherein $X_1$ is 9-fluorenylmethyloxycarbonyl.

5. The compounds of claim 2 wherein $X_1$ is p-anisyldiphenylmethyl.

6. The compounds of claim 2 wherein $X_1$ is triphenylmethyl.

7. The compounds of claim 2 wherein $X_1$ is N-trifluoroacetylglycol.

8. The compounds of claim 2 wherein B is thymine.

9. The compounds of claim 2 wherein B is uracil.

10. The compounds of claim 2 wherein $R_2$ is methyl.

11. The compounds of claim 2 wherein $R_2$ is beta-cyanoethyl.

12. The compounds of claim 2 wherein $R_1$ is methyl.

13. The compounds of claim 2 wherein $R_1$ is isopropyl.

14. The compounds of claim 2 wherein $R_1$ is morpholino.

15. The compounds of claim 2 wherein B is thymine and $X_1$ is trifluoroacetyl.

16. The compounds of claim 2 wherein B is thymine and $X_1$ is 9-fluorenylmethyloxycarbonyl.

17. The compounds of claim 2 wherein B is thymine and $X_1$ is p-anisyldiphenylmethyl.

18. The compounds of claim 2 wherein B is thymine and $X_1$ is triphenylmethyl.

19. The compounds of claim 2 wherein B is thymine and $X_1$ is N-trifluolroacetylglycyl.

20. The compounds of claim 2 wherein B is uracil and $X_1$ is trifluoroacetyl.

21. The compounds of claim 2 wherein B is uracil and $X_1$ is 9-fluorenylmethyloxycarbonyl.

22. The compounds of claim 2 wherein B is uracil and $X_1$ is p-anisyldiphenylmethyl.

23. The compounds of claim 2 wherein B is uracil and $X_1$ is triphenylmethyl.

24. The compounds of claim 2 wherein B is uracil and $X_1$ is N-trifluoroacetylglycyl.

25. 5'-N-(9-fluorenylmethyloxycarbonyl)-5'-amino-5'-deoxythymidine-3'-O-methyl-N,N-diisopropylamino phosphoramidite having the formula:

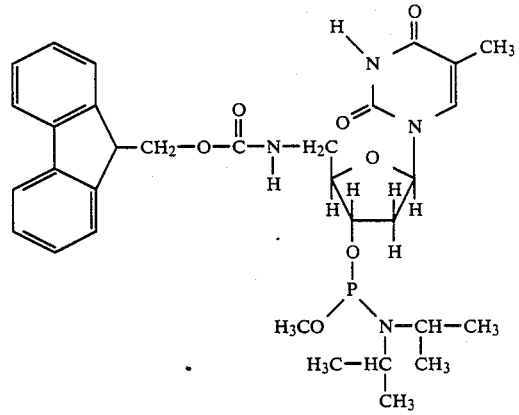

26. 5'-N-p-anisyldiphenylmethyl-5'-amino-5'-dioxythymidine-3'-O-beta-cyanoethyl-N,N-diisopropylamino phosphoramidite having the formula:

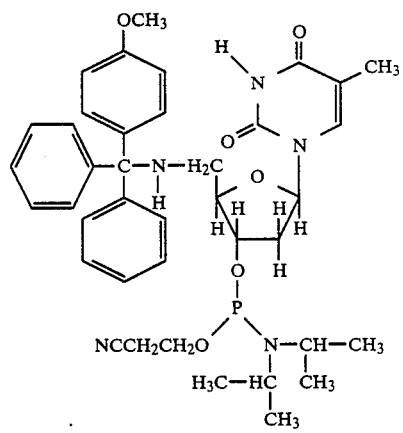

27. 5'-N-(9-fluorenylmethyloxycarbonyl)-5'-amino-5'-deoxythymidine-3'-O-beta-cyanoethyl-N,N-diisopropylamino phosphoramidite.

28. 5'-N-(9-fluorenylmethyloxycarbonyl)-5'-amino-5'-deoxythymidine-3'-O-methyl-N,N-dimethylamino phosphoramidite.

29. 5'-N-(9-fluorenylmethyloxycarbonyl)-5'-amino-5'-deoxythymidine-3'-O-beta-cyanoethyl-N,N-dimethylamino phosphoramidite.

30. 5'-N-p-anisyldiphenylmethyl-5'-amino-5'-deoxythymidine-3'-O-methyl-N,N-diisopropylamino phosphoramidite.

31. 5'-N-p-anisyldiphenylmethyl-5'-amino-5'-deoxythymidine-3'-O-beta-cyanoethyl-N,N-dimethylamino phosphoramidite.

32. 5'-N-p-anisyldiphenylmethyl-5'-amino-5'-deoxythymidine-3'-O-methyl-N,N-dimethylamino phosphoramidite.

33. 5'-N-p-triphenylmethyl-5'-amino-5'-deoxythymidine-3'-O-beta-cyanoethyl-N,N-diisopropylamino phosphoramidite.

34. Protected 5'-amino nucleoside phosphoramidites having the formula:

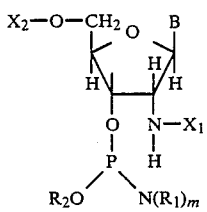

wherein B is selected from the group consisting of thymine and uracil; $X_1$ is selected from trifluoroacetyl, 9-fluorenylmethyloxycarbonyl, p-anisyldiphenylmethyl, triphenylmethyl, and protected amino acyl having the formula:

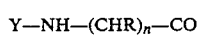

wherein Y is selected from the group consisting of trifluoroacetyl, 9-fluorenylmethyloxycarbonyl, p-anisyldiphenylmethyl, and triphenylmethyl;

R is an amino acid side chain or hydrogen when $n=1$; and R is hydrogen when n is an integer from 2 to 100;

$R_1$ is selected from the group consisting of lower alkyl (in which case $m=2$) and heterocyclic (in which case $m=1$), and $R_2$ is selected from the group consisting of methyl, beta-cyanoethyl, p-nitrophenethyl, o-chlorophenyl, or p-chlorophenyl; and $X_2$ is a hydroxyl protecting group selected from triphenylmethyl, p-anisyl-diphenylmethyl, di-p-anisylphenylmethyl, and 9-phenylxanthenyl.

35. The compounds of claim 34 wherein $X_1$ is trifluoroacetyl.

36. The compounds of claim 34 wherein $X_1$ is 9-fluorenylmethyloxycarbonyl.

37. The compounds of claim 34 wherein $X_1$ is N-trifluoroacetylglycol.

38. The compounds of claim 34 wherein B is uracil.

39. The compounds of claim 34 wherein $R_1$ is methyl.

40. The compounds of claim 34 wherein $R_1$ is isopropyl.

41. The compounds of claim 34 wherein $R_1$ is morpholino.

42. The compounds of claim 34 wherein $R_2$ is methyl.

43. The compounds of claim 34 wherein $R_2$ is beta-cynaoethyl.

44. The compounds of claim 34 wherein B is uracil and $X_1$ is trifluoroacetyl.

45. The compounds of claim 34 wherein B is uracil and $X_1$ is fluorenylmethyloxycarbonyl.

46. The compounds of claim 34 wherein B is uracil and $X_1$ is N-trifluoroacetylglycyl.

47. 5'-O-di-p-anisylphenylmethyl-2'-N -trifluoroacetyl-2 -amino-2'-deoxyuridine-3'-O-methyl-N, N-diisopropylamino phosphoramidite having the formula:

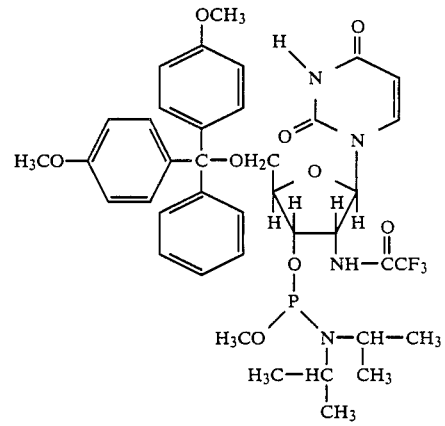

48. 5'-O-di-p-anisylphenylmethyl-2'-N-(N-trifluoroacetylglycol) -2'-amino-2'-deoxyuridine-3'-O-methyl-N,N-diisopropylamino phosphoramidite having the formula:

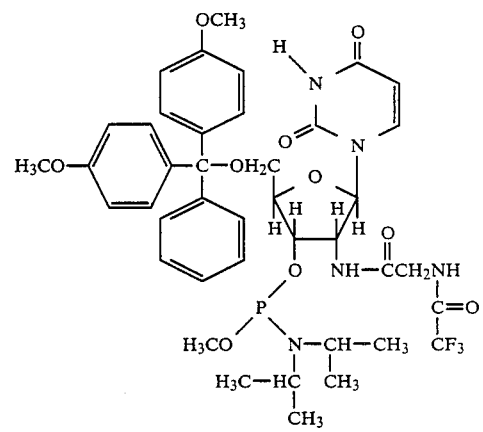

49. 5'-O-di-p-anisylphenylmethyl-2'-N-trifluoroacetyl -2'-amino-2'-deoxyuridine-3 -O-beta-cyanoethyl-N, N-diisopropylamino phosphoramidite.

50. 5'-O-di-p-anisylphenylmethyl-2'-N-(N-trifluoroacetylglycol) -2'-amino-2'-deoxyuridine-3'-O-beta-cyanoethyl-N, N-diisopropylamino phosphoramidite.

51. Protected 2'-amino-nucleoside phosphoramidites having the formula:

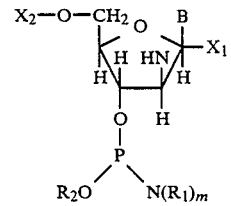

wherein B is selected from the the group consisting of thymine and uracil; $X_1$ is selected from trifluoroacetyl, 9-fluorenylmethyloxycarbonyl, p-anisyldiphenylmethyl, triphenylmethyl, and protected amino acyl having the formula:

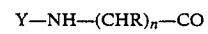

wherein Y is selected from the group consisting of trofluoroacetyl, 9- fluorenylmethoxycarbonyl, p-anisylphenylmethyl, and triphenylmethyl;

R is an amino acid side chain or hydrogen when n=1; and R is hydrogen when n is an integer from 2 to 100;

$R_1$ is selected from the group consisting of lower alkyl (in which case m=2) and heterocyclic (in which case m=1), and $R_2$ is selected from the group consisting of methyl, beta-cyanoethyl, p-nitrophenethyl, O-chlorophenyl, or p-chlorophenyl; and $X_2$ is a hydroxyl protecting group selected from triphenylmethyl, p-anisyl-diphenylmethyl, di-p-anisylphenylmethyl, and 9-phenylxanthenyl.

52. The compounds of claim 51 wherein $X_1$ is trifluoroacetyl.

53. The compounds of claim 51 wherein $X_1$ is 9-fluorenylmethyloxycarbonyl.

54. The compounds of claim 51 wherein $X_1$ is N-trifluoroacetylglycyl.

55. The compounds of claim 51 wherein B is uracil.

56. The compounds of claim 51 wherein $R_1$ is methyl.

57. The compounds of claim 49 wherein $R_1$ is isopropyl.

58. The compounds of claim 49 wherein $R_1$ is morpholino.

59. The compounds of claim 49 wherein $R_2$ is methyl.

60. The compounds of claim 49 wherein $R_2$ is beta-cyanoethyl.

61. The compounds of claim 49 wherein B is uracil and $X_1$ is trifluoroacetyl.

62. The compounds of claim 49 wherein B is uracil and $X_1$ is fluorenylmethyloxycarbonyl.

63. The compounds of claim 49 wherein B is uracil and $X_1$ is N-trifluoroacetylglycyl.

64. 5'-O-di-p-anisylphenylmethyl-2'-N-trifluoroacetyl-2'-amino-2'-deoxy-ara-uridine-3'-O-methyl-N, N-diiso-propylamino phosphoramidite.

65. 5'-O-di-p-anisylphenylmethyl-2'-N-(N-trifluoroacetylglycol)-2'-amino-2'-deoxy-ara-uridine-3'-O-methyl-N,N-diiso-propylamino phosphoramidite.

66. 5'-O-di-p-anisylphenylmethyl-2'-N-trifluoroacetyl-2'-amino-2'-deoxy-ara-uridine-3'-O-beta-cyanoethyl-N,N-diiso-propylamino phosphoramidite.

67. 5'-O-di-p-anisylphenylmethyl-2'-N-(N-trifluoroacetylglycol)-2'-amino-2'-deoxy-ara-uridine-3'-O-beta cyanoethyl-N,N-diisopropylamino phosphoramidite.

* * * * *

UNITED STATES PATENT AND TRADEMARK OFFICE
CERTIFICATE OF CORRECTION

PATENT NO.  : 4,849,513

DATED       : July 18, 1989

INVENTOR(S) : Lloyd M. Smith et al

It is certified that error appears in the above-identified patent and that said Letters Patent is hereby corrected as shown below:

On the title page inventor should read

— (75) Inventors: Lloyd M. Smith, South Pasadena;
Steven Fung, Palo Alto;
Robert J. Kaiser, Jr., Glendale, all
of Calif.--.

Signed and Sealed this

Twenty-third Day of October, 1990

Attest:

HARRY F. MANBECK, JR.

*Attesting Officer*  *Commissioner of Patents and Trademarks*